(12) United States Patent
Shalton, IV et al.

(10) Patent No.: US 7,721,936 B2
(45) Date of Patent: May 25, 2010

(54) INTERLOCK AND SURGICAL INSTRUMENT INCLUDING SAME

(75) Inventors: Frederick E. Shalton, IV, New Vienna, OH (US); James R. Giordano, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 592 days.

(21) Appl. No.: 11/651,788

(22) Filed: Jan. 10, 2007

(65) Prior Publication Data

US 2008/0167670 A1    Jul. 10, 2008

(51) Int. Cl.
*A61B 17/068* (2006.01)
(52) U.S. Cl. .................... 227/180.1; 227/19; 227/176.1
(58) Field of Classification Search .................... 227/19, 227/176.1, 175.1, 179.1, 180.1; 606/219, 606/139
See application file for complete search history.

(56) References Cited

U.S. PATENT DOCUMENTS

| | | | |
|---|---|---|---|
| 3,490,675 A | 1/1970 | Green et al. | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,500,024 A | 2/1985 | DiGiovanni et al. | |
| 4,505,273 A | 3/1985 | Braun et al. | |
| 4,505,414 A | 3/1985 | Filipi | |
| 4,522,327 A | 6/1985 | Korthoff et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,610,383 A | 9/1986 | Rothfuss et al. | |
| 4,629,107 A | 12/1986 | Fedotov et al. | |
| 4,655,222 A | 4/1987 | Florez et al. | |

(Continued)

FOREIGN PATENT DOCUMENTS

CA    2458946 A1    3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner*—Scott A. Smith

(57) ABSTRACT

A surgical instrument is disclosed. The instrument includes an end effector comprising a moveable cutting instrument to cut an object and a motor coupled to the end effector. The motor actuates the cutting instrument in response to a current therethrough, causing the cutting instrument to move between a proximal-most position and a distal-most position. The instrument includes an interlock coupled to the end effector and to the motor to prevent actuation of the cutting instrument based on the current through the motor.

12 Claims, 20 Drawing Sheets

U.S. PATENT DOCUMENTS

| | | |
|---|---|---|
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,821,939 A | 4/1989 | Green |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,383,880 A | 1/1995 | Hooven |
| 5,395,033 A | 3/1995 | Byrne et al. |
| 5,397,324 A | 3/1995 | Carroll et al. |
| 5,425,745 A | 6/1995 | Green et al. |
| 5,433,721 A | 7/1995 | Hooven et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A | 1/1996 | Blewett |
| 5,484,451 A | 1/1996 | Akopov et al. |
| 5,485,947 A | 1/1996 | Olson et al. |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,518,163 A | 5/1996 | Hooven |
| 5,518,164 A | 5/1996 | Hooven |
| 5,529,235 A | 6/1996 | Boiarski et al. |
| 5,535,934 A | 7/1996 | Boiarski et al. |
| 5,543,119 A | 8/1996 | Sutter et al. |
| 5,553,765 A | 9/1996 | Knodel et al. |
| 5,554,169 A | 9/1996 | Green et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,702,408 A | 12/1997 | Wales et al. |
| 5,704,534 A | 1/1998 | Huitema et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,807,393 A | 9/1998 | Williamson, IV et al. |
| 5,817,093 A | 10/1998 | Williamson, IV et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,868,760 A | 2/1999 | McGuckin, Jr. |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,915,616 A | 6/1999 | Viola et al. |
| 5,919,198 A | 7/1999 | Graves, Jr. et al. |
| 5,941,442 A | 8/1999 | Geiste et al. |
| 5,954,259 A | 9/1999 | Viola et al. |

| | | | |
|---|---|---|---|
| 6,010,054 A | 1/2000 | Johnson et al. |
| 6,024,741 A | 2/2000 | Williamson, IV et al. |
| 6,032,849 A | 3/2000 | Mastri et al. |
| 6,045,560 A | 4/2000 | McKean et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,119,913 A | 9/2000 | Adams et al. |
| 6,126,058 A | 10/2000 | Adams et al. |
| 6,171,330 B1 | 1/2001 | Benchetrit |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,330,965 B1 | 12/2001 | Milliman et al. |
| 6,387,113 B1 | 5/2002 | Hawkins et al. |
| RE37,814 E | 8/2002 | Allgeyer |
| 6,436,107 B1 | 8/2002 | Wang et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,988 B2 | 10/2003 | Weadock |
| 6,644,532 B2 | 11/2003 | Green et al. |
| 6,666,875 B1 | 12/2003 | Sakurai et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,793,652 B1 | 9/2004 | Whitman et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,108,695 B2 | 9/2006 | Witt et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,128,253 B2 | 10/2006 | Mastri et al. |
| 7,140,527 B2 | 11/2006 | Ehrenfels et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 2002/0117534 A1 | 8/2002 | Green et al. |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2004/0006372 A1 | 1/2004 | Racenet et al. |

| | | | | | | |
|---|---|---|---|---|---|---|
| 2004/0034369 A1 | 2/2004 | Sauer et al. | | 2008/0029574 A1 | 2/2008 | Shelton et al. |
| 2004/0094597 A1 | 5/2004 | Whitman et al. | | 2008/0029575 A1 | 2/2008 | Shelton et al. |
| 2004/0108357 A1 | 6/2004 | Milliman et al. | | 2008/0029576 A1 | 2/2008 | Shelton et al. |
| 2004/0116952 A1 | 6/2004 | Sakurai et al. | | 2008/0035701 A1 | 2/2008 | Racenet et al. |
| 2004/0164123 A1 | 8/2004 | Racenet et al. | | 2008/0041917 A1 | 2/2008 | Racenet et al. |
| 2004/0167572 A1 | 8/2004 | Roth et al. | | 2008/0078800 A1 | 4/2008 | Hess et al. |
| 2004/0173659 A1 | 9/2004 | Green et al. | | 2008/0078801 A1 | 4/2008 | Shelton et al. |
| 2004/0222268 A1 | 11/2004 | Bilotti et al. | | 2008/0078802 A1 | 4/2008 | Hess et al. |
| 2004/0232201 A1 | 11/2004 | Wenchell et al. | | 2008/0078803 A1 | 4/2008 | Shelton et al. |
| 2004/0243151 A1 | 12/2004 | Demmy et al. | | 2008/0078804 A1 | 4/2008 | Shelton et al. |
| 2004/0254608 A1 | 12/2004 | Huitema et al. | | 2008/0078806 A1 | 4/2008 | Omaits et al. |
| 2005/0059997 A1 | 3/2005 | Bauman et al. | | 2008/0078807 A1 | 4/2008 | Hess et al. |
| 2005/0103819 A1 | 5/2005 | Racenet et al. | | 2008/0078808 A1 | 4/2008 | Hess et al. |
| 2005/0119669 A1 | 6/2005 | Demmy | | 2008/0082115 A1 | 4/2008 | Morgan et al. |
| 2005/0125009 A1 | 6/2005 | Perry et al. | | 2008/0082124 A1 | 4/2008 | Hess et al. |
| 2005/0131390 A1 | 6/2005 | Heinrich et al. | | 2008/0082125 A1 | 4/2008 | Murray et al. |
| 2005/0143759 A1 | 6/2005 | Kelly | | 2008/0082126 A1 | 4/2008 | Murray et al. |
| 2005/0184121 A1 | 8/2005 | Heinrich | | 2008/0164296 A1 | 7/2008 | Shelton et al. |
| 2005/0187576 A1 | 8/2005 | Whitman et al. | | 2008/0167522 A1 | 7/2008 | Giordano et al. |
| 2005/0189397 A1 | 9/2005 | Jankowski | | 2008/0167644 A1 | 7/2008 | Shelton et al. |
| 2005/0216055 A1 | 9/2005 | Scirica et al. | | 2008/0167671 A1 | 7/2008 | Giordano et al. |
| 2005/0263563 A1 | 12/2005 | Racenet et al. | | 2008/0167672 A1 | 7/2008 | Giordano et al. |
| 2005/0274768 A1 | 12/2005 | Cummins et al. | | 2008/0167736 A1 | 7/2008 | Swayze et al. |
| 2006/0011699 A1 | 1/2006 | Olson et al. | | 2008/0169328 A1 | 7/2008 | Shelton |
| 2006/0025812 A1 | 2/2006 | Shelton, IV | | 2008/0169329 A1 | 7/2008 | Shelton et al. |
| 2006/0047307 A1 | 3/2006 | Ortiz et al. | | 2008/0169330 A1 | 7/2008 | Shelton et al. |
| 2006/0049229 A1 | 3/2006 | Milliman et al. | | 2008/0169331 A1 | 7/2008 | Shelton et al. |
| 2006/0052825 A1 | 3/2006 | Ransick et al. | | 2008/0169332 A1 | 7/2008 | Shelton et al. |
| 2006/0085033 A1 | 4/2006 | Criscuolo et al. | | 2008/0169333 A1 | 7/2008 | Shelton et al. |
| 2006/0100643 A1 | 5/2006 | Laufer et al. | | 2008/0210738 A1 | 9/2008 | Shelton et al. |
| 2006/0108393 A1 | 5/2006 | Heinrich et al. | | 2008/0237296 A1 | 10/2008 | Boudreaux et al. |
| 2006/0151567 A1 | 7/2006 | Roy | | 2008/0296343 A1 | 12/2008 | Schall et al. |
| 2006/0180634 A1 | 8/2006 | Shelton, IV et al. | | 2008/0296345 A1 | 12/2008 | Shelton, IV et al. |
| 2006/0226196 A1 | 10/2006 | Hueil et al. | | 2008/0296346 A1 | 12/2008 | Shelton, IV et al. |
| 2006/0241692 A1 | 10/2006 | McGuckin, Jr. et al. | | 2008/0296347 A1 | 12/2008 | Shelton, IV et al. |
| 2006/0273135 A1 | 12/2006 | Beetel | | 2008/0300579 A1 | 12/2008 | Broehl et al. |
| 2006/0278680 A1 | 12/2006 | Viola et al. | | 2008/0300580 A1 | 12/2008 | Shelton, IV et al. |
| 2006/0278681 A1 | 12/2006 | Viola et al. | | 2008/0300613 A1 | 12/2008 | Shelton, IV et al. |
| 2006/0289602 A1 | 12/2006 | Wales et al. | | 2008/0308601 A1 | 12/2008 | Timm et al. |
| 2007/0023477 A1 | 2/2007 | Whitman et al. | | 2008/0308602 A1 | 12/2008 | Timm et al. |
| 2007/0034668 A1 | 2/2007 | Holsten et al. | | 2008/0308603 A1 | 12/2008 | Shelton, IV et al. |
| 2007/0045379 A1 | 3/2007 | Shelton, IV | | 2008/0308606 A1 | 12/2008 | Timm et al. |
| 2007/0084897 A1 | 4/2007 | Shelton, IV et al. | | 2008/0308607 A1 | 12/2008 | Timm et al. |
| 2007/0102452 A1 | 5/2007 | Shelton, IV et al. | | 2008/0308608 A1 | 12/2008 | Prommersberger |
| 2007/0102453 A1 | 5/2007 | Morgan et al. | | 2008/0314954 A1 | 12/2008 | Boudreaux |
| 2007/0102472 A1 | 5/2007 | Shelton, IV | | 2008/0314955 A1 | 12/2008 | Boudreaux et al. |
| 2007/0102473 A1 | 5/2007 | Shelton, IV et al. | | 2008/0314956 A1 | 12/2008 | Boudreaux |
| 2007/0102474 A1 | 5/2007 | Shelton, IV et al. | | 2008/0314957 A1 | 12/2008 | Boudreaux |
| 2007/0106317 A1 | 5/2007 | Shelton, IV et al. | | 2008/0314961 A1 | 12/2008 | Boudreaux et al. |
| 2007/0114261 A1 | 5/2007 | Ortiz et al. | | 2008/0314962 A1 | 12/2008 | Boudreaux |
| 2007/0158385 A1 | 7/2007 | Hueil et al. | | 2009/0001121 A1 | 1/2009 | Hess et al. |
| 2007/0170225 A1 | 7/2007 | Shelton, IV et al. | | 2009/0001123 A1 | 1/2009 | Morgan et al. |
| 2007/0175949 A1 | 8/2007 | Shelton, IV et al. | | 2009/0001124 A1 | 1/2009 | Hess et al. |
| 2007/0175950 A1 | 8/2007 | Shelton, IV et al. | | 2009/0001125 A1 | 1/2009 | Hess et al. |
| 2007/0175951 A1 | 8/2007 | Shelton, IV et al. | | 2009/0001126 A1 | 1/2009 | Hess et al. |
| 2007/0175953 A1 | 8/2007 | Shelton, IV et al. | | 2009/0001128 A1 | 1/2009 | Weisenburgh, II et al. |
| 2007/0175955 A1 | 8/2007 | Shelton, IV et al. | | 2009/0001130 A1 | 1/2009 | Hess et al. |
| 2007/0175956 A1 | 8/2007 | Swayze et al. | | 2009/0005807 A1 | 1/2009 | Hess et al. |
| 2007/0175957 A1 | 8/2007 | Shelton, IV et al. | | 2009/0005808 A1 | 1/2009 | Hess et al. |
| 2007/0175958 A1 | 8/2007 | Shelton, IV et al. | | 2009/0005809 A1 | 1/2009 | Hess et al. |
| 2007/0175959 A1 | 8/2007 | Shelton, IV et al. | | 2009/0012556 A1 | 1/2009 | Boudreaux et al. |
| 2007/0175964 A1 | 8/2007 | Shelton, IV et al. | | 2009/0076534 A1 | 3/2009 | Shelton, IV et al. |
| 2007/0179476 A1 | 8/2007 | Shelton, IV et al. | | 2009/0200355 A1 | 8/2009 | Baxter, III et al. |
| 2007/0181632 A1 | 8/2007 | Milliman | | 2009/0206123 A1 | 8/2009 | Doll et al. |
| 2007/0194079 A1 | 8/2007 | Hueil et al. | | 2009/0206124 A1 | 8/2009 | Hall et al. |
| 2007/0194080 A1 | 8/2007 | Swayze et al. | | 2009/0206125 A1 | 8/2009 | Huitema et al. |
| 2007/0194081 A1 | 8/2007 | Hueil et al. | | 2009/0206126 A1 | 8/2009 | Huitema et al. |
| 2007/0194082 A1 | 8/2007 | Morgan et al. | | 2009/0206128 A1 | 8/2009 | Hueil et al. |
| 2007/0233053 A1 | 10/2007 | Shelton, IV et al. | | 2009/0206129 A1 | 8/2009 | Doll et al. |
| 2007/0246505 A1 | 10/2007 | Pace-Floridia et al. | | 2009/0206130 A1 | 8/2009 | Hall et al. |
| 2007/0295780 A1 | 12/2007 | Shelton et al. | | 2009/0206131 A1 | 8/2009 | Weisenburgh, II et al. |
| 2008/0029570 A1 | 2/2008 | Shelton et al. | | 2009/0206132 A1 | 8/2009 | Hueil et al. |
| 2008/0029573 A1 | 2/2008 | Shelton et al. | | 2009/0206133 A1 | 8/2009 | Morgan et al. |

| | | | | | | |
|---|---|---|---|---|---|---|
| 2009/0206134 | A1 | 8/2009 | Swayze et al. | EP | 1086713 B1 | 5/2004 |
| 2009/0206135 | A1 | 8/2009 | Hall et al. | EP | 1426012 A1 | 6/2004 |
| 2009/0206136 | A1 | 8/2009 | Moore et al. | EP | 0888749 B1 | 9/2004 |
| 2009/0206137 | A1 | 8/2009 | Hall et al. | EP | 1477119 A1 | 11/2004 |
| 2009/0206138 | A1 | 8/2009 | Smith et al. | EP | 1479345 A1 | 11/2004 |
| 2009/0206139 | A1 | 8/2009 | Hall et al. | EP | 1479347 A1 | 11/2004 |
| 2009/0206140 | A1 | 8/2009 | Scheib et al. | EP | 1479348 A1 | 11/2004 |
| 2009/0206141 | A1 | 8/2009 | Huitema et al. | EP | 1520521 A1 | 4/2005 |
| 2009/0206142 | A1 | 8/2009 | Huitema et al. | EP | 1520523 A1 | 4/2005 |
| 2009/0206143 | A1 | 8/2009 | Huitema et al. | EP | 1520525 A1 | 4/2005 |
| 2009/0206144 | A1 | 8/2009 | Doll et al. | EP | 1522264 A1 | 4/2005 |
| 2009/0209946 | A1 | 8/2009 | Swayze et al. | EP | 1550408 A1 | 7/2005 |
| 2009/0255974 | A1 | 10/2009 | Viola | EP | 1557129 A1 | 7/2005 |
| 2009/0255978 | A1 | 10/2009 | Viola et al. | EP | 1064883 B1 | 8/2005 |
| | | | | EP | 1157666 B1 | 9/2005 |

FOREIGN PATENT DOCUMENTS

| | | | | | | |
|---|---|---|---|---|---|---|
| | | | | EP | 1621138 A2 | 2/2006 |
| CA | 2512960 | A1 | 1/2006 | EP | 1621139 A2 | 2/2006 |
| CA | 2514274 | A1 | 1/2006 | EP | 1621141 A2 | 2/2006 |
| DE | 273689 | C | 5/1914 | EP | 1621145 A2 | 2/2006 |
| DE | 1775926 | A | 1/1972 | EP | 1652481 A2 | 5/2006 |
| DE | 9412228 | U | 9/1994 | EP | 1382303 B1 | 6/2006 |
| DE | 19924311 | A1 | 11/2000 | EP | 1045672 B1 | 8/2006 |
| DE | 69328576 | T2 | 1/2001 | EP | 1617768 B1 | 8/2006 |
| DE | 20112837 | U1 | 10/2001 | EP | 1702567 A2 | 9/2006 |
| DE | 20121753 | U1 | 4/2003 | EP | 1129665 B1 | 11/2006 |
| DE | 10314072 | A1 | 10/2004 | EP | 1256317 B1 | 12/2006 |
| EP | 0122046 | A1 | 10/1984 | EP | 1728473 A1 | 12/2006 |
| EP | 0033548 | B1 | 5/1986 | EP | 1728475 A2 | 12/2006 |
| EP | 0276104 | A2 | 7/1988 | EP | 1479346 B1 | 1/2007 |
| EP | 0605351 | B1 | 11/1988 | EP | 1484024 B1 | 1/2007 |
| EP | 0639349 | A2 | 2/1994 | EP | 1754445 A2 | 2/2007 |
| EP | 0324636 | B1 | 3/1994 | EP | 1759812 A1 | 3/2007 |
| EP | 0593920 | A1 | 4/1994 | EP | 1769756 A1 | 4/2007 |
| EP | 0600182 | A2 | 6/1994 | EP | 1769758 A1 | 4/2007 |
| EP | 0630612 | A1 | 12/1994 | EP | 1785097 A2 | 5/2007 |
| EP | 0634144 | A1 | 1/1995 | EP | 1790293 A2 | 5/2007 |
| EP | 0646356 | A2 | 4/1995 | EP | 1300117 B1 | 8/2007 |
| EP | 0646357 | A1 | 4/1995 | EP | 1813199 A1 | 8/2007 |
| EP | 0653189 | A2 | 5/1995 | EP | 1813207 A1 | 8/2007 |
| EP | 0669104 | A1 | 8/1995 | EP | 1872727 A1 | 1/2008 |
| EP | 0679367 | A2 | 11/1995 | EP | 1839596 A2 | 2/2008 |
| EP | 0392547 | B1 | 12/1995 | EP | 1897502 A1 | 3/2008 |
| EP | 0685204 | A1 | 12/1995 | EP | 1759645 B1 | 11/2008 |
| EP | 0699418 | A1 | 3/1996 | EP | 1749486 B1 | 3/2009 |
| EP | 0702937 | A1 | 3/1996 | FR | 999646 A | 2/1952 |
| EP | 0705571 | A1 | 4/1996 | FR | 1112936 A | 3/1956 |
| EP | 0484677 | B2 | 6/1996 | FR | 2765794 A | 1/1999 |
| EP | 0541987 | B1 | 7/1996 | GB | 939929 A | 10/1963 |
| EP | 0667119 | B1 | 7/1996 | GB | 1210522 A | 10/1970 |
| EP | 0770355 | A1 | 5/1997 | GB | 2336214 A | 10/1999 |
| EP | 0503662 | B1 | 6/1997 | JP | 6007357 A | 1/1994 |
| EP | 0625335 | B1 | 11/1997 | JP | 7051273 A | 2/1995 |
| EP | 0552423 | B1 | 1/1998 | JP | 8033641 A | 2/1996 |
| EP | 0592244 | B1 | 1/1998 | JP | 8229050 A | 9/1996 |
| EP | 0648476 | B1 | 1/1998 | JP | 2000287987 A | 10/2000 |
| EP | 0676173 | B1 | 9/1998 | JP | 2001286477 A | 10/2001 |
| EP | 0603472 | B1 | 11/1998 | JP | 2002369820 A | 12/2002 |
| EP | 0878169 | A1 | 11/1998 | JP | 2005505322 T | 2/2005 |
| EP | 0879742 | A1 | 11/1998 | JP | 2005103293 A | 4/2005 |
| EP | 0760230 | B1 | 2/1999 | RU | 2187249 C2 | 8/2002 |
| EP | 0537572 | B1 | 6/1999 | RU | 2225170 C2 | 3/2004 |
| EP | 0552050 | B1 | 5/2000 | SU | 1377053 A1 | 2/1988 |
| EP | 1090592 | A1 | 4/2001 | SU | 1561964 A1 | 5/1990 |
| EP | 1256318 | B1 | 5/2001 | SU | 1722476 A1 | 3/1992 |
| EP | 0908152 | B1 | 1/2002 | WO | WO 93/08755 A1 | 5/1993 |
| EP | 0872213 | B1 | 5/2002 | WO | WO 95/18572 A1 | 7/1995 |
| EP | 1238634 | A2 | 9/2002 | WO | WO 95/23557 A1 | 9/1995 |
| EP | 0656188 | B1 | 1/2003 | WO | WO 95/29639 A1 | 11/1995 |
| EP | 0829235 | B1 | 6/2003 | WO | WO 96/35464 A1 | 11/1996 |
| EP | 0813843 | B1 | 10/2003 | WO | WO 97/34533 A1 | 9/1997 |
| EP | 0741996 | B1 | 2/2004 | WO | WO 97/39688 A2 | 10/1997 |
| EP | 0705570 | B1 | 4/2004 | WO | WO 98/30153 A1 | 7/1998 |
| | | | | WO | WO 99/12483 A1 | 3/1999 |

| | | | |
|---|---|---|---|
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |
| WO | WO 2007/018898 A2 | 2/2007 |
| WO | WO 2007/121579 A1 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

Partial European Search Report contained in the publication of Application No. 08250102.4, which published on Jul. 16, 2008 (40 pages).

INTERLOCK AND SURGICAL INSTRUMENT INCLUDING SAME

CROSS-REFERENCE TO RELATED APPLICATIONS

The present application is related to the following, concurrently-filed U.S. Patent Applications, which are incorporated herein by reference in their entirety:

(1) U.S. patent application Ser. No. 11/651,715, entitled "SURGICAL INSTRUMENT WITH WIRELESS COMMUNICATION BETWEEN CONTROL UNIT AND SENSOR TRANSPONDERS," by J. Giordano et al.;

(2) U.S. patent application Ser. No. 11/651,807, entitled "SURGICAL INSTRUMENT WITH WIRELESS COMMUNICATION BETWEEN CONTROL UNIT AND REMOTE SENSOR," by J. Giordano et al.;

(3) U.S. patent application Ser. No. 11/651,806, entitled "SURGICAL INSTRUMENT WITH ELEMENTS TO COMMUNICATE BETWEEN CONTROL UNIT AND END EFFECTOR," by J. Giordano et al.;

(4) U.S. patent application Ser. No. 11/651,768, entitled "PREVENTION OF CARTRIDGE REUSE IN A SURGICAL INSTRUMENT," by F. Shelton et al.;

(5) U.S. patent application Ser. No. 11/651,785, entitled "POST-STERILIZATION PROGRAMMING OF SURGICAL INSTRUMENTS," by J. Swayze et al.; and (6) U.S. patent application Ser. No. 11/651,785, entitled "SURGICAL INSTRUMENT WITH ENHANCED BATTERY PERFORMANCE," by F. Shelton et al.

FIELD OF THE INVENTION

The disclosed invention relates generally and in various embodiments to surgical stapling and cutting instruments structured and configured for applying lines of staples from a staple cartridge into tissue while cutting the tissue between the applied staple lines. More particularly the disclosed invention relates to an interlock for use in motorized surgical stapling and cutting instruments that prevents cutting of the tissue when the staple cartridge is not installed, or when the staple cartridge is installed but spent.

BACKGROUND

Endoscopic surgical instruments are often preferred over traditional open surgical devices since a smaller incision tends to reduce post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Advantageously, the design of the end effector may be such that it can be reused with the surgical stapler. For instance, one patient may need a series of severing and stapling operations. Replacing an entire end effector for each operation tends to be economically inefficient, especially if the end effector is built for strength and reliability over repeated operations. To that end, the staple cartridge is typically configured to be disposable and is fitted into the end effector prior to each operation of the surgical stapler.

An example of a surgical stapler suitable for endoscopic applications is described in U.S. Pat. No. 5,465,895, entitled "SURGICAL STAPLER INSTRUMENT" to Knodel et al., which discloses an endocutter with distinct closing and firing actions. Thereby, an operator is able to close the jaw members upon tissue to position the tissue prior to firing. Once the operator has determined that the jaw members are properly gripping tissue, the operator can then fire the surgical stapler with either a single firing stroke or multiple firing strokes, depending on the device. Firing the surgical stapler causes severing and stapling of the tissue. The simultaneous severing and stapling avoids complications that may arise when performing such actions sequentially with different surgical tools that respectively only sever and staple.

One specific advantage of being able to close upon tissue before firing is that the operator is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Because the actuating force (i.e., the "force-to-fire", or FTF) necessary to close the jaws and simultaneously perform the cutting and stapling operation may be considerable, a manually-powered cutting and stapling instrument such as that described above may not be utilizable by otherwise qualified operators who are unable to generate the required FTF. Accordingly, powered cutting and stapling instruments have been developed for decreasing the force-to-fire (FTF). Such instruments typically incorporate motors or other actuating mechanisms suitable for supplementing or replacing operator-generated force for performing the cutting and stapling operation.

Although powered instruments provide numerous advantages, it is desirable to prevent inadvertent firing of the instrument under certain conditions. For example, firing the instrument without having a staple cartridge installed, or firing the instrument having an installed but spent (e.g., previously fired) staple cartridge, may result in cutting of tissue without simultaneous stapling to minimize bleeding. Interlocks for preventing powered endocutter operation under such conditions have heretofore utilized electronic sensors in the end effector for determining whether an unspent staple cartridge has been installed in the end effector. U.S. patent application Ser. No. 11/343,439 entitled "ELECTRONIC INTERLOCKS AND SURGICAL INSTRUMENT INCLUDING SAME" to Swayze et al., the disclosure of which is incorporated herein by reference, discloses the use of electronic sensors disposed within the end effector for determining if an unspent staple cartridge has been installed. The sensors may include switches connected in series with a motor or other electrically-powered actuation mechanism such that current flow necessary for generating the actuating force is prevented when the staple cartridge is not installed, or when the staple cartridge is installed but spent. Although such electronic interlocks are effective, placement of sensors in the end effector and routing electrical cabling between the sensors and motor electronics (typically housed in the instrument handle) increases instrument complexity and cost.

Although the use of mechanical interlocks in end effectors for preventing inadvertent firing is known and avoids complexities associated with end effector electronics, such mechanisms have heretofore been limited to manually powered endocutters. In particular, such mechanisms may not have the mechanical strength to resist the firing force generated by electrically-powered actuation mechanisms. Additionally, even if a mechanical interlock is capable of withstanding the firing force, the resulting physical stresses may be transmitted to other instrument components and cause unacceptable wear or damage.

Consequently, a significant need exists for an interlock for use in powered cutting and stapling instruments that prevents inadvertent firing (e.g., cutting but not stapling) while avoiding complexities of sensor-equipped end effectors and deleterious physical stresses that may otherwise result from the use of conventional mechanical interlocks.

SUMMARY

This application discloses a surgical cutting and stapling instrument according to various embodiments. The instrument includes an end effector comprising a moveable cutting instrument to cut an object and a motor to actuate the cutting instrument in response to a current therethrough. The actuation of the cutting instrument causes the cutting instrument to move between a proximal-most position and a distal-most position. The instrument further includes an interlock coupled to the end effector and to the motor to prevent actuation of the cutting instrument based on the current through the motor.

This application further discloses a method for preventing operation of a surgical instrument. The surgical instrument is configured for removably receiving an expendable staple cartridge and comprises a moveable cutting instrument and a motor to actuate the cutting instrument in response to a current therethrough. The method comprises mechanically blocking actuation of the cutting instrument by the motor in the absence of an unexpended staple cartridge in the instrument, detecting the current through the motor resulting from the blocked actuation of the cutting instrument, and interrupting the current through the motor based on the detected current.

DRAWINGS

Various embodiments of the present invention are described herein by way of example in conjunction with the following figures, wherein.

DETAILED DESCRIPTION

Figure 1:
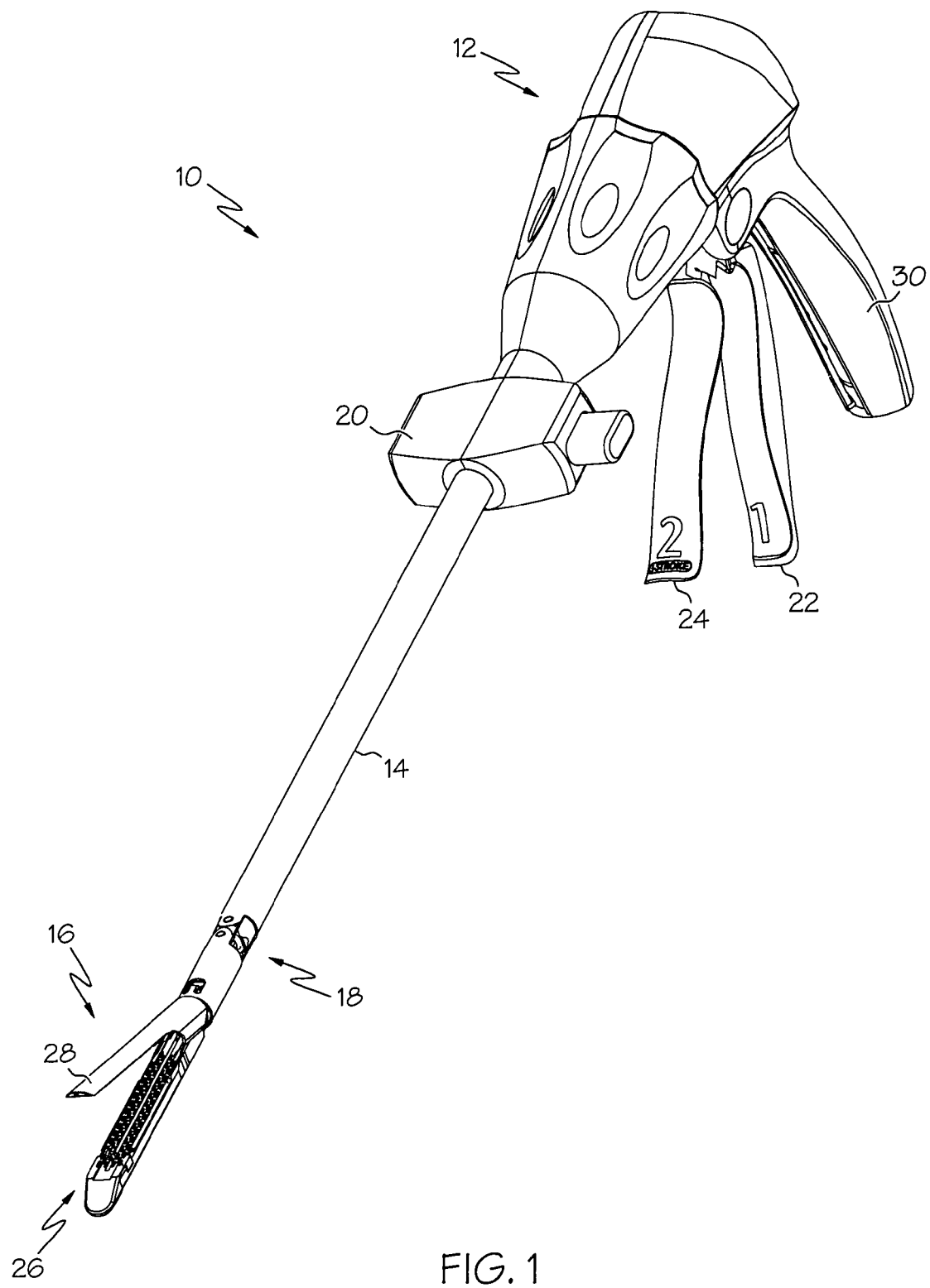
FIGS. 1 and 2 are perspective views of a surgical cutting and fastening instrument according to various embodiments of the present invention.
Figure 2:
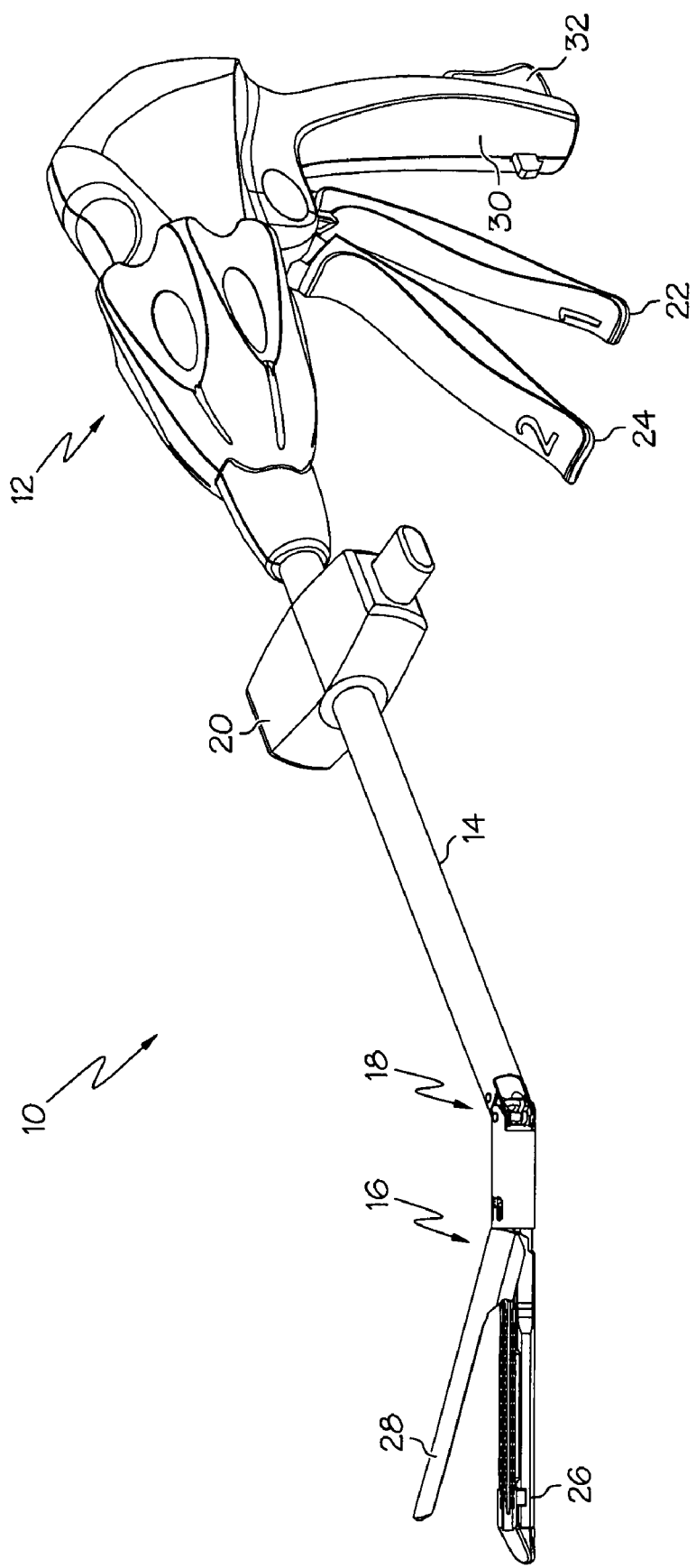

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 12, a shaft 14, and an articulating end effector 16 pivotally connected to the shaft 14 at an articulation pivot 18. An articulation control 20 may be provided adjacent to the handle 12 to effect rotation of the end effector 16 about the articulation pivot 18. In the illustrated embodiment, the end effector 16 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 12 of the instrument 10 may include a closure trigger 22 and a firing trigger 24 for actuating the end effector 16. It will be appreciated that instruments having end effectors directed to different surgical tasks may have different numbers or types of triggers or other suitable controls for operating the end effector 16. The end effector 16 is shown separated from the handle 12 by a preferably elongate shaft 14. In one embodiment, a operator of the instrument 10 may articulate the end effector 16 relative to the shaft 14 by utilizing the articulation control 20 as described in more detail in pending U.S. patent application Ser. No. 11/329,020 entitled "SURGICAL INSTRUMENT HAVING AN ARTICULATING END EFFECTOR" to Hueil et al., which is incorporated herein by reference.

The end effector 16 includes in this example, among other things, a staple channel 26 and a pivotally translatable clamping member, such as an anvil 28, which are maintained at a spacing that assures effective stapling and severing of tissue clamped in the end effector 16. The handle 12 includes a pistol grip 30 towards which a closure trigger 22 is pivotally drawn by the operator to cause clamping or closing of the anvil 28 toward the staple channel 26 of the end effector 16 to thereby clamp tissue positioned between the anvil 28 and the channel 26. The firing trigger 24 is farther outboard of the closure trigger 22. Once the closure trigger 22 is locked in the closure position as further described below, the firing trigger 24 may rotate slightly toward the pistol grip 30 so that it can be reached by the operator using one hand. The operator may then pivotally draw the firing trigger 24 toward the pistol grip 30 to cause the stapling and severing of clamped tissue in the end effector 16. In other embodiments, different types of clamping members besides the anvil 28 may be used, such as, for example, an opposing jaw, etc.

It will be appreciated that the terms "proximal" and "distal" are used herein with reference to a operator gripping the handle 12 of an instrument 10. Thus, the end effector 16 is distal with respect to the more proximal handle 12. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 22 may be actuated first. Once the operator is satisfied with the positioning of the end effector 16, the operator may draw back the closure trigger 22 to its fully closed, locked position proximate to the pistol grip 30. The firing trigger 24 may then be actuated. The firing trigger 24 returns to the open position (shown in FIGS. 1 and 2) when the operator removes pressure, as described more fully below. A release button 32 on the handle 12, when depressed, may release the locked closure trigger 22. Various configurations for locking and unlocking the closure trigger 22 using the release button 32 are described in pending U.S. patent application Ser. No. 11/343,573 entitled "MOTOR-DRIVEN SURGICAL CUTTING AND FASTENING INSTRUMENT WITH LOADING FORCE FEEDBACK" to Shelton, IV et al., which is incorporated herein by reference.

Figure 3:
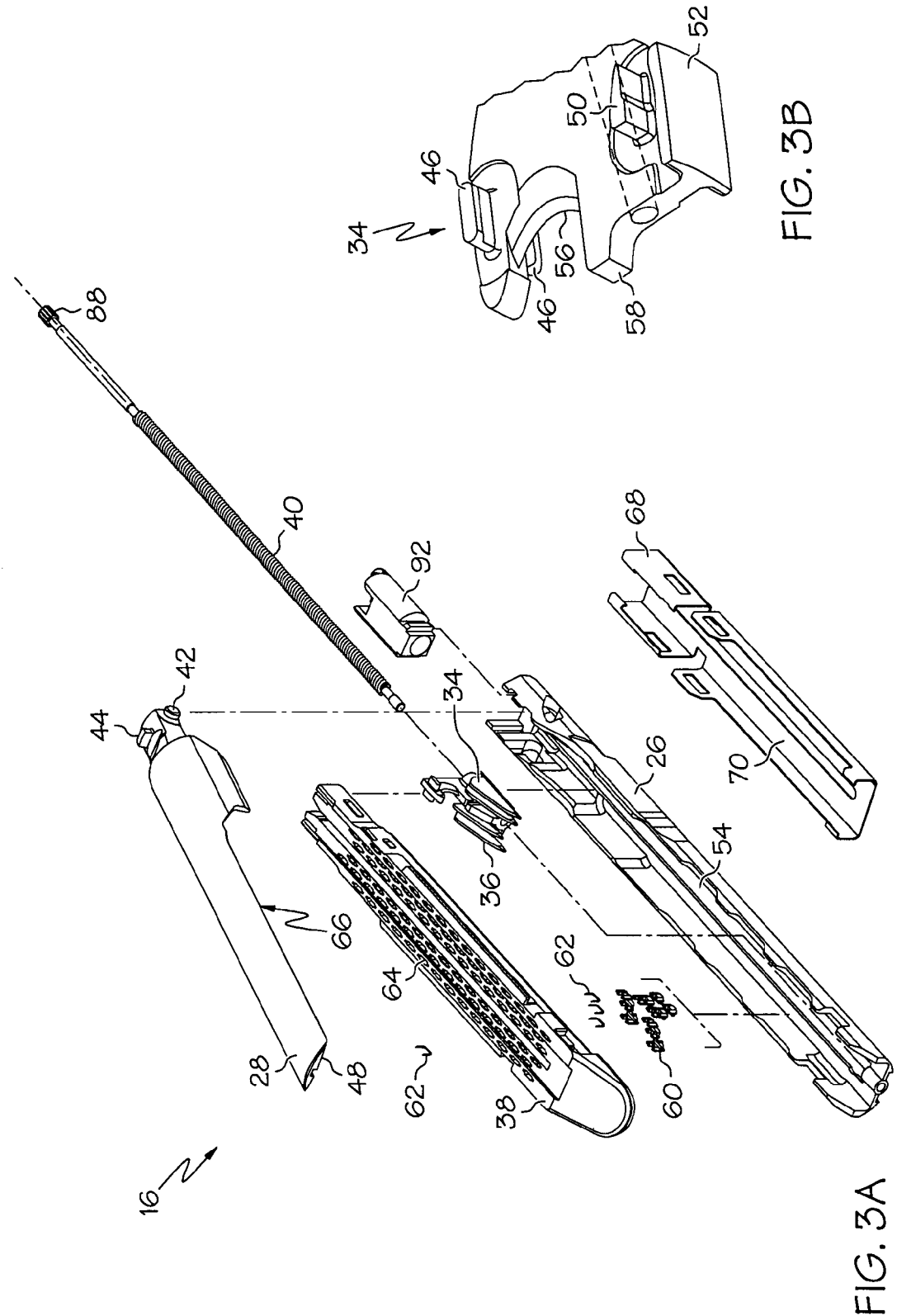
FIG. 3A is an exploded view of the end effector according to various embodiments of the present invention.
FIG. 3B is a perspective view of the cutting instrument of FIG. 3A.

FIG. 3A is an exploded view of the end effector 16 according to various embodiments. As shown in the illustrated embodiment, the end effector 16 may include, in addition to the previously-mentioned channel 26 and anvil 28, a cutting instrument 34, a sled 36, a staple cartridge 38 that is removably seated (e.g., installed) in the channel 26, and a helical screw shaft 40, and FIG. 3B is a perspective view of the cutting instrument of FIG. 3A.

The anvil 28 may be pivotably opened and closed at a pivot point 42 connected to the proximate end of the channel 26. The anvil 28 may also include a tab 44 at its proximate end that is inserted into a component of the mechanical closure system (described further below) to open and close the anvil 28. When the closure trigger 22 is actuated, that is, drawn in by an operator of the instrument 10, the anvil 28 may pivot about the pivot point 42 into the clamped or closed position. If clamping of the end effector 16 is satisfactory, the operator may actuate the firing trigger 24, which, as explained in more detail below, causes the cutting instrument 34 to travel longitudinally along the channel 26.

As shown, the cutting instrument 34 includes upper guide pins 46 that enter an anvil slot 48 in the anvil 28 to verify and assist in maintaining the anvil 28 in a closed state during staple formation and severing. Spacing between the channel 26 and anvil 28 is further maintained by the cutting instrument 34 by having middle pins 50 slide along the top surface of the channel 26 while a bottom foot 52 opposingly slides along the undersurface of the channel 26, guided by a longitudinal opening 54 in the channel 26. A distally presented cutting surface 56 between the upper guide pins 46 and middle pins 50 severs clamped tissue while distally-presented surface 58 actuates the staple cartridge 38 by progressively driving the sled 36 from an unfired position to a fired position. Actuation of the staple cartridge 38 causes staple drivers 60 to cam upwardly, driving staples 62 out of upwardly open staple holes 64 formed in the staple cartridge 38. The staples 62 are subsequently formed against a staple forming undersurface 66 of the anvil 28. A staple cartridge tray 68 encompasses from the bottom the other components of the staple cartridge 38 to hold them in place. The staple cartridge tray 68 includes a rearwardly open slot 70 that overlies the longitudinal opening 54 in the channel 26. A lower surface of the staple cartridge 38 and an upward surface of the channel 26 form a firing drive slot 200 (FIG. 6) through which the middle pins 50 pass during distal and proximal movement of the cutting instrument 34. The sled 36 may be an integral component of the staple cartridge 38 such that when the cutting instrument 34 retracts following the cutting operation, the sled 36 does not retract. U.S. Pat. No. 6,978,921, entitled "SURGICAL STAPLING INSTRUMENT INCORPORATING AN E-BEAM FIRING MECHANISM" to Shelton, IV et al., which is incorporated herein by reference, provides more details about such two-stroke cutting and fastening instruments.

It should be noted that although the embodiments of the instrument 10 described herein employ an end effector 16 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTOSURGICAL HEMOSTATIC DEVICE WITH RECESSED AND/OR OFFSET ELECTRODES" to Yates et al., both of which are incorporated herein by reference, disclose cutting instruments that uses RF energy to fasten the severed tissue. U.S. patent application Ser. No. 11/267,811 entitled "SURGICAL STAPLING INSTRUMENTS STRUCTURED FOR DELIVERY OF MEDICAL AGENTS" to Morgan et al., and U.S. patent application Ser. No. 11/267,383 entitled "SURGICAL STAPLING INSTRUMENTS STRUCTURED FOR PUMP-ASSISTED DELIVERY OF MEDICAL AGENTS" to Shelton IV et al., both of which are also incorporated herein by reference, disclose cutting instruments that uses adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 4:
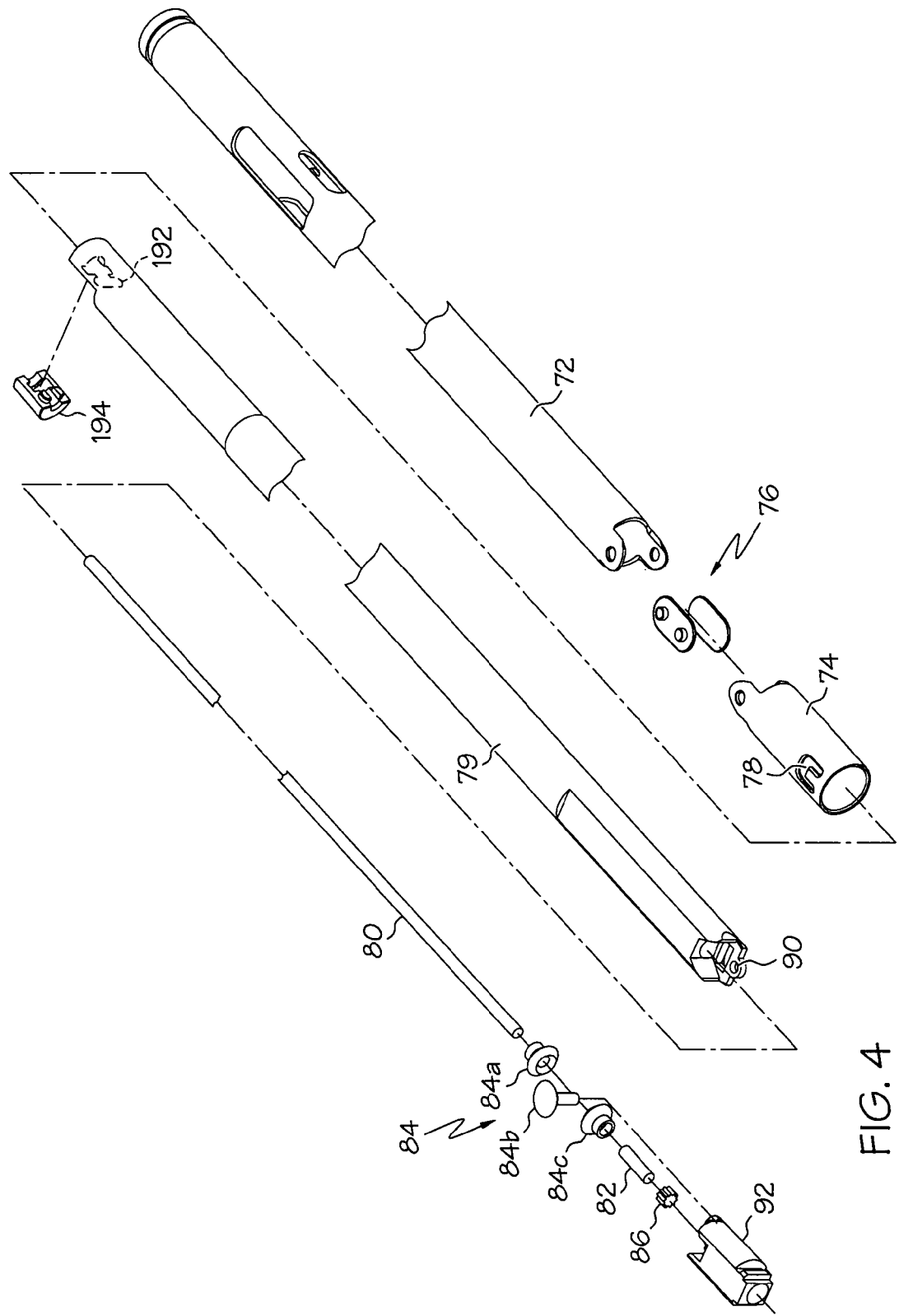
FIGS. 4 and 5 are exploded views of an end effector and shaft of the instrument according to various embodiments of the present invention.
Figure 5:
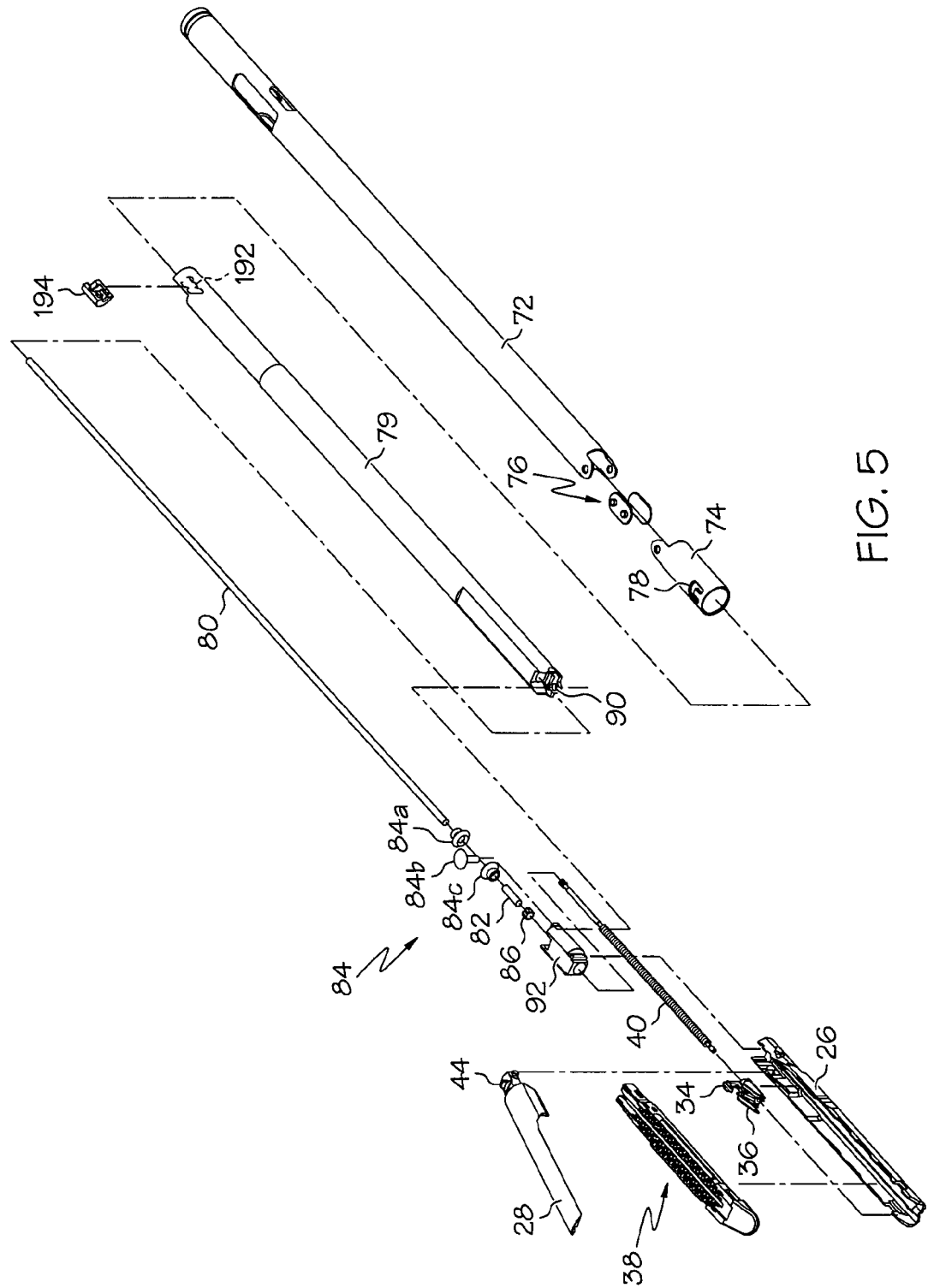
Figure 6:
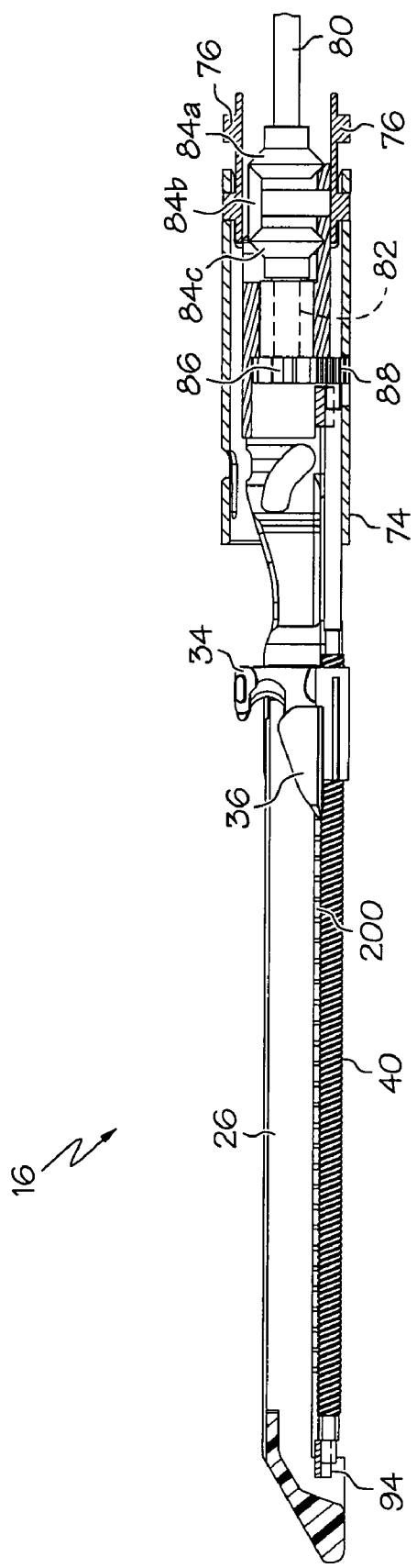
FIG. 6 is a side view of the end effector according to various embodiments of the present invention.
Figure 7:
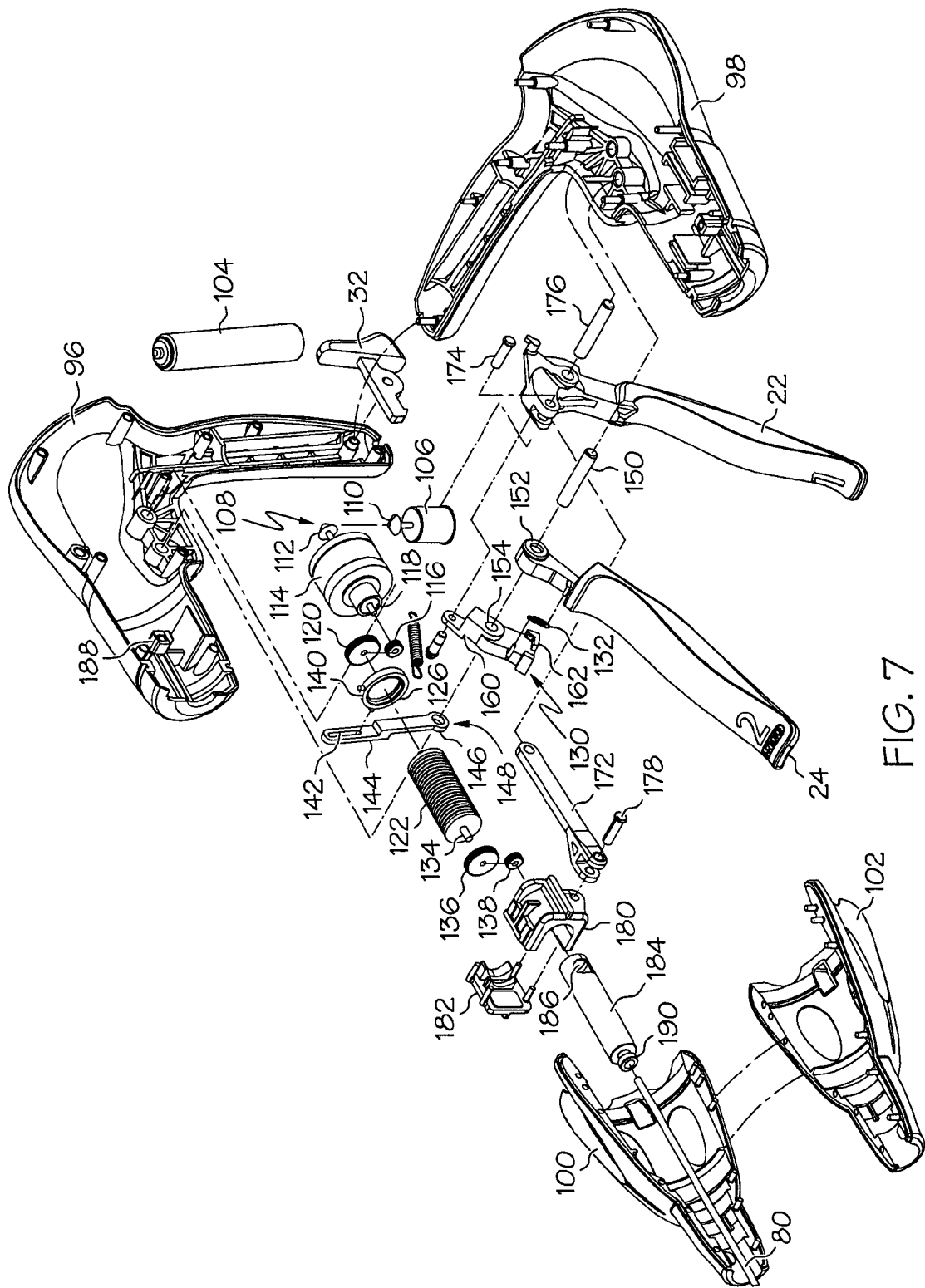
FIG. 7 is an exploded view of the handle of the instrument according to various embodiments of the present invention.

FIGS. 4 and 5 are exploded views and FIG. 6 is a side view of the end effector 16 and shaft 14 according to various embodiments. As shown in the illustrated embodiment, the shaft 14 may include a proximate closure tube 72 and a distal closure tube 74 pivotably linked by a pivot links 76. The distal closure tube 74 includes an opening 78 into which the tab 44 on the anvil 28 is inserted in order to open and close the anvil 28, as further described below. Disposed inside the closure tubes 72, 74 may be a proximate spine tube 79. Disposed inside the proximate spine tube 79 may be a main rotational (or proximate) drive shaft 80 that communicates with a secondary (or distal) drive shaft 82 via a bevel gear assembly 84. The secondary drive shaft 82 is connected to a drive gear 86 that engages a proximate drive gear 88 of the helical screw shaft 40. The vertical bevel gear 84b may sit and pivot in an opening 90 in the distal end of the proximate spine tube 79. A distal spine tube 92 may be used to enclose the secondary drive shaft 82 and the drive gears 86, 88. Collectively, the main drive shaft 80, the secondary drive shaft 82, and the articulation assembly (e.g., the bevel gear assembly 84a-c) are sometimes referred to herein as the "main drive shaft assembly."

A bearing 94 (FIG. 6) positioned at a distal end of the staple channel 26 receives the helical screw shaft 40, allowing the helical screw shaft 40 to freely rotate with respect to the channel 26. The helical screw shaft 40 may interface a threaded opening (not shown) of the cutting instrument 34 such that rotation of the helical screw shaft 40 causes the cutting instrument 34 to translate distally or proximately (depending on the direction of the rotation) through the staple channel 26. Accordingly, when the main drive shaft 80 is caused to rotate by actuation of the firing trigger 24 (as explained in further detail below), the bevel gear assembly 84a-c causes the secondary drive shaft 82 to rotate, which in turn, because of the engagement of the drive gears 86, 88, causes the helical screw shaft 40 to rotate, which causes the cutting instrument 34 to travel longitudinally along the channel 26 to cut any tissue clamped within the end effector 16. The sled 36 may be made of, for example, plastic, and may have a sloped distal surface. As the sled 36 traverses the channel 26, the sloped distal surface may cam the staple drivers 60 upward, which in turn push up or drive the staples 62 in the staple cartridge 38 through the clamped tissue and against the staple forming undersurface 66 of the anvil 28, thereby stapling the severed tissue. When the cutting instrument 34 is retracted, the cutting instrument 34 and the sled 36 may become disengaged, thereby leaving the sled 36 at the distal end of the channel 26.

FIGS. 7-10 illustrate an exemplary embodiment of a motor-driven endocutter, and in particular the handle 12 thereof, that provides operator-feedback regarding the deployment and loading force of the cutting instrument 34 in the end effector 16. In addition, the embodiment may use power provided by the operator in retracting the firing trigger 24 to power the device (a so-called "power assist" mode). As shown in the illustrated embodiment, the handle 12 includes exterior lower side pieces 96, 98 and exterior upper side pieces 100, 102 that fit together to form, in general, the exterior of the handle 12. A battery 104 may be provided in the pistol grip portion 30 of the handle 12. The battery 64 may be constructed according to any suitable construction or chemistry including, for example, a Li-ion chemistry such as LiCoO2 or LiNiO2, a Nickel Metal Hydride chemistry, etc. The battery 104 powers a motor 106 disposed in an upper portion of the pistol grip portion 30 of the handle 12. According to various embodiments, the motor 106 may be a DC brushed driving motor having a maximum rotation of approximately 5000 to 100,000 RPM. The motor 106 may drive a 90-degree bevel gear assembly 108 comprising a first bevel gear 110 and a second bevel gear 112. The bevel gear assembly 108 may drive a planetary gear assembly 114. The planetary gear assembly 114 may include a pinion gear 116 connected to a drive shaft 118. The pinion gear 116 may drive a mating ring gear 120 that drives a helical gear drum 122 via a drive shaft 124. A ring 126 may be threaded on the helical gear drum 122. Thus, when the motor 106 rotates, the ring 126 is caused to travel along the helical gear drum 122 by means of the interposed bevel gear assembly 108, planetary gear assembly 114 and ring gear 120.

The handle 12 may also include a run motor sensor 128 in communication with the firing trigger 24 to detect when the firing trigger 24 has been drawn in (or "closed") toward the pistol grip portion 30 of the handle 12 by the operator to thereby actuate the cutting/stapling operation by the end effector 16. The sensor 128 may be a proportional sensor such as, for example, a rheostat or variable resistor. When the firing trigger 24 is drawn in, the sensor 128 detects the movement, and sends an electrical signal indicative of the voltage (or power) to be supplied to the motor 106. When the sensor 128 is a variable resistor or the like, the rotation of the motor 106 may be generally proportional to the amount of movement of the firing trigger 24. That is, if the operator only draws or closes the firing trigger 24 in a little bit, the rotation of the motor 106 is relatively low. When the firing trigger 24 is fully drawn in (or in the fully closed position), the rotation of the motor 106 is at its maximum. In other words, the harder the operator pulls on the firing trigger 24, the more voltage is applied to the motor 106, causing a greater rate of rotation. In another embodiment, for example, a microcontroller (e.g., the microcontroller 250 of FIG. 29) may output a PWM control signal to the motor 106 based on the input from the sensor 128 in order to control the motor 106.

The handle 12 may include a middle handle piece 130 adjacent to the upper portion of the firing trigger 24. The handle 12 also may comprise a bias spring 132 connected between posts on the middle handle piece 130 and the firing trigger 24. The bias spring 132 may bias the firing trigger 24 to its fully open position. In that way, when the operator releases the firing trigger 24, the bias spring 132 will pull the firing trigger 24 to its open position, thereby removing actuation of the sensor 128, thereby stopping rotation of the motor 106. Moreover, by virtue of the bias spring 132, any time an operator closes the firing trigger 24, the operator will experience resistance to the closing operation, thereby providing the operator with feedback as to the amount of rotation exerted by the motor 106. Further, the operator could stop retracting the firing trigger 24 to thereby remove force from the sensor 128, to thereby stop the motor 106. As such, the operator may stop the deployment of the end effector 16, thereby providing a measure of control of the cutting/fastening operation to the operator.

The distal end of the helical gear drum 122 includes a distal drive shaft 134 that drives a ring gear 136, which mates with a pinion gear 138. The pinion gear 138 is connected to the main drive shaft 80 of the main drive shaft assembly. In that way, rotation of the motor 106 causes the main drive shaft assembly to rotate, which causes actuation of the end effector 16, as described above.

The ring 126 threaded on the helical gear drum 122 may include a post 140 that is disposed within a slot 142 of a slotted arm 144. The slotted arm 144 has an opening 146 its opposite end 148 that receives a pivot pin 150 that is connected between the handle exterior side pieces 96, 98. The pivot pin 150 is also disposed through an opening 152 in the firing trigger 24 and an opening 154 in the middle handle piece 130.

In addition, the handle 12 may include a reverse motor (or end-of-stroke) sensor 156 and a stop motor (or beginning-of-stroke) sensor 158. In various embodiments, the reverse motor sensor 156 may be a normally-open limit switch located at the distal end of the helical gear drum 122 such that the ring 126 threaded on the helical gear drum 122 contacts and closes the reverse motor sensor 156 when the ring 126 reaches the distal end of the helical gear drum 122. The reverse motor sensor 156, when closed, sends a signal to the motor 106 to reverse its rotation direction, thereby retracting the cutting instrument 34 of the end effector 16 following a cutting operation.

The stop motor sensor 158 may be, for example, a normally-closed limit switch. In various embodiments, it may be located at the proximate end of the helical gear drum 122 so that the ring 126 opens the switch 158 when the ring 126 reaches the proximate end of the helical gear drum 122.

In operation, when an operator of the instrument 10 pulls back the firing trigger 24, the sensor 128 detects the deployment of the firing trigger 24 and sends a signal to the motor 106 to cause forward rotation of the motor 106 at, for example, a rate proportional to how hard the operator pulls back the firing trigger 24. The forward rotation of the motor 106 in turn causes the ring gear 120 at the distal end of the planetary gear assembly 114 to rotate, thereby causing the helical gear drum 122 to rotate, causing the ring 126 threaded on the helical gear drum 122 to travel distally along the helical gear drum 122. The rotation of the helical gear drum 122 also drives the main drive shaft assembly as described above, which in turn causes deployment of the cutting instrument 34 in the end effector 16. That is, the cutting instrument 34 and sled 36 are caused to traverse the channel 26 longitudinally, thereby cutting tissue clamped in the end effector 16. Also, the stapling operation of the end effector 16 is caused to happen in embodiments where a stapling-type end effector is used.

By the time the cutting/stapling operation of the end effector 16 is complete, the ring 126 on the helical gear drum 122 will have reached the distal end of the helical gear drum 122, thereby causing the reverse motor sensor 156 to be actuated, which sends a signal to the motor 106 to cause the motor 106 to reverse its rotation. This in turn causes the cutting instrument 34 to retract, and also causes the ring 126 on the helical gear drum 122 to move back to the proximate end of the helical gear drum 122.

Figure 8:
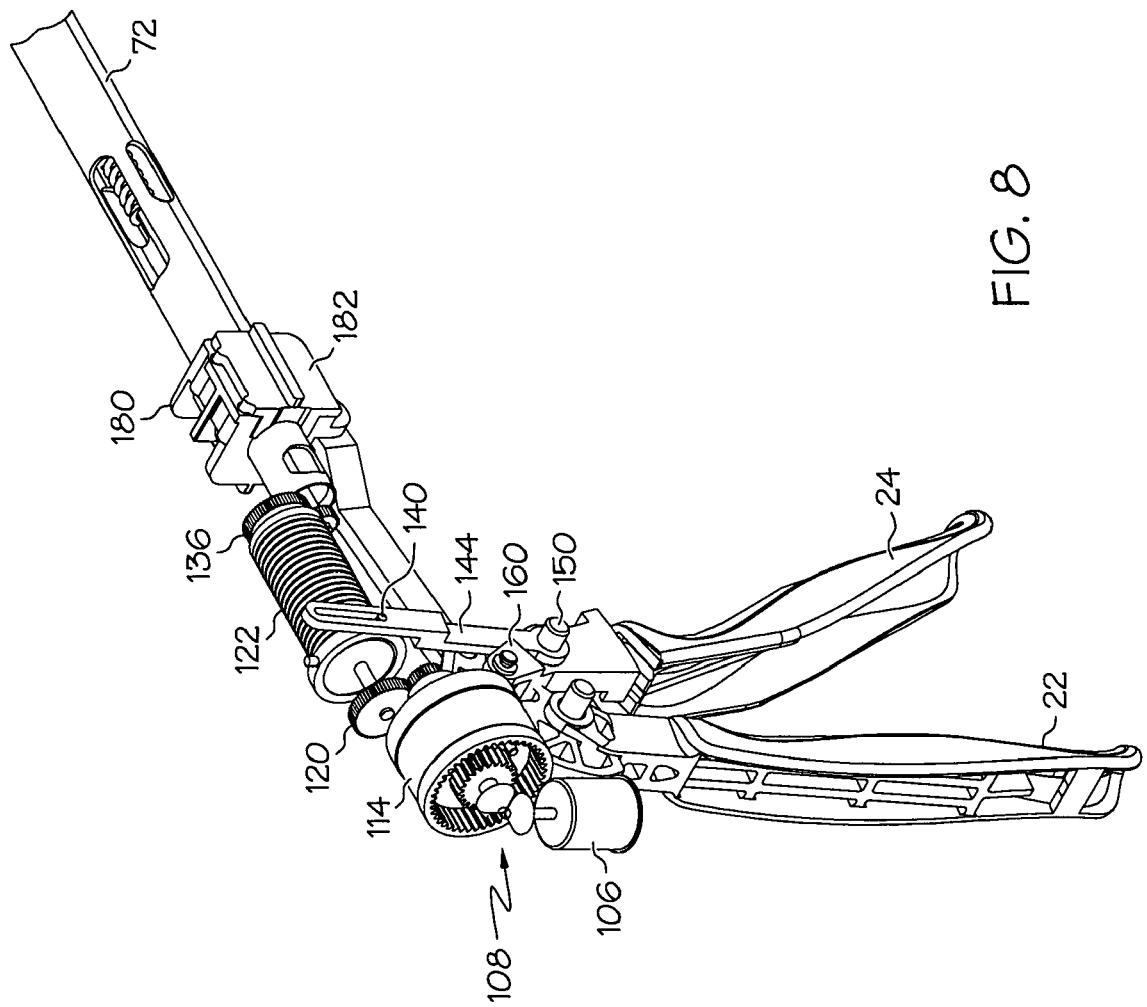
FIGS. 8 and 9 are partial perspective views of the handle according to various embodiments of the present invention.
Figure 9:
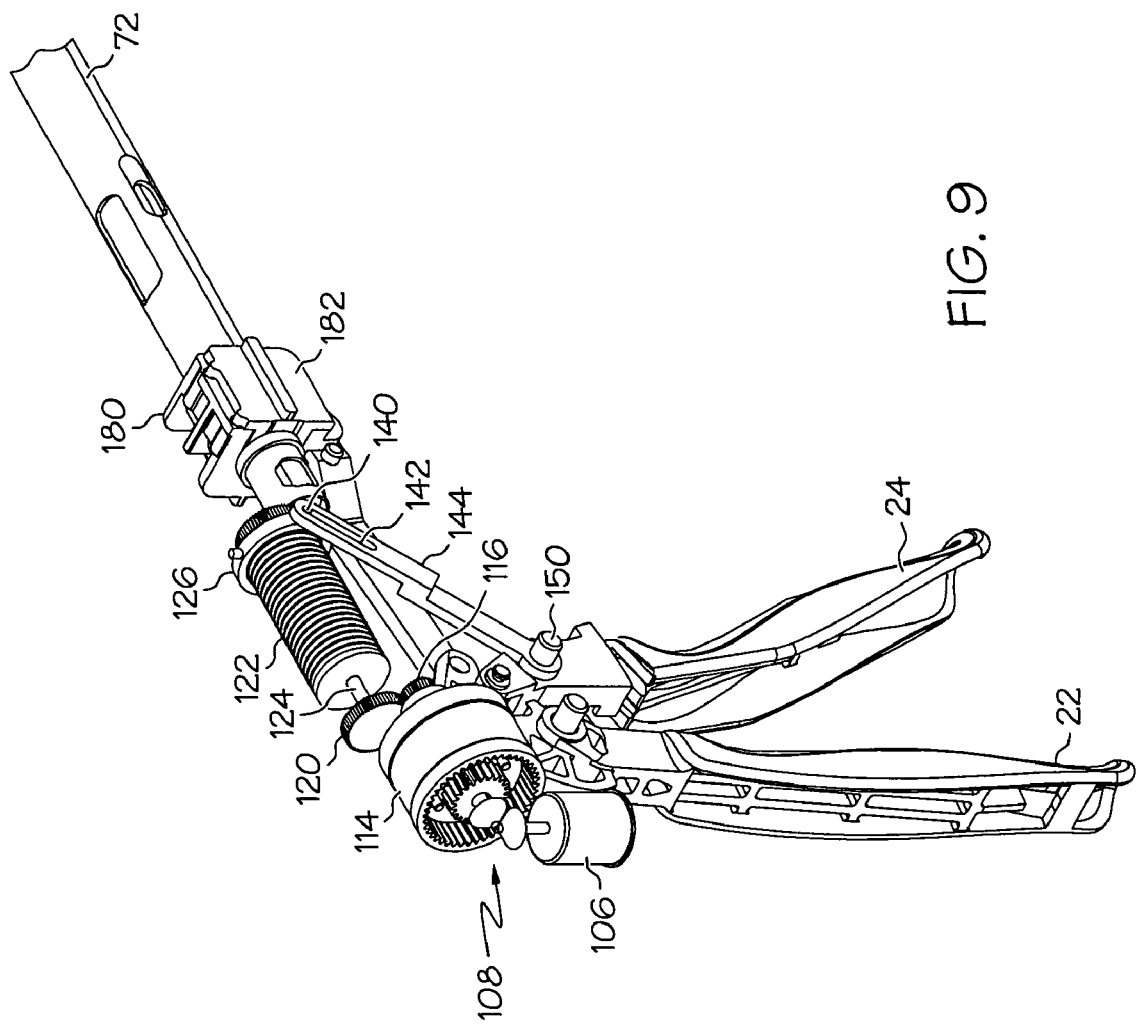
Figure 10:
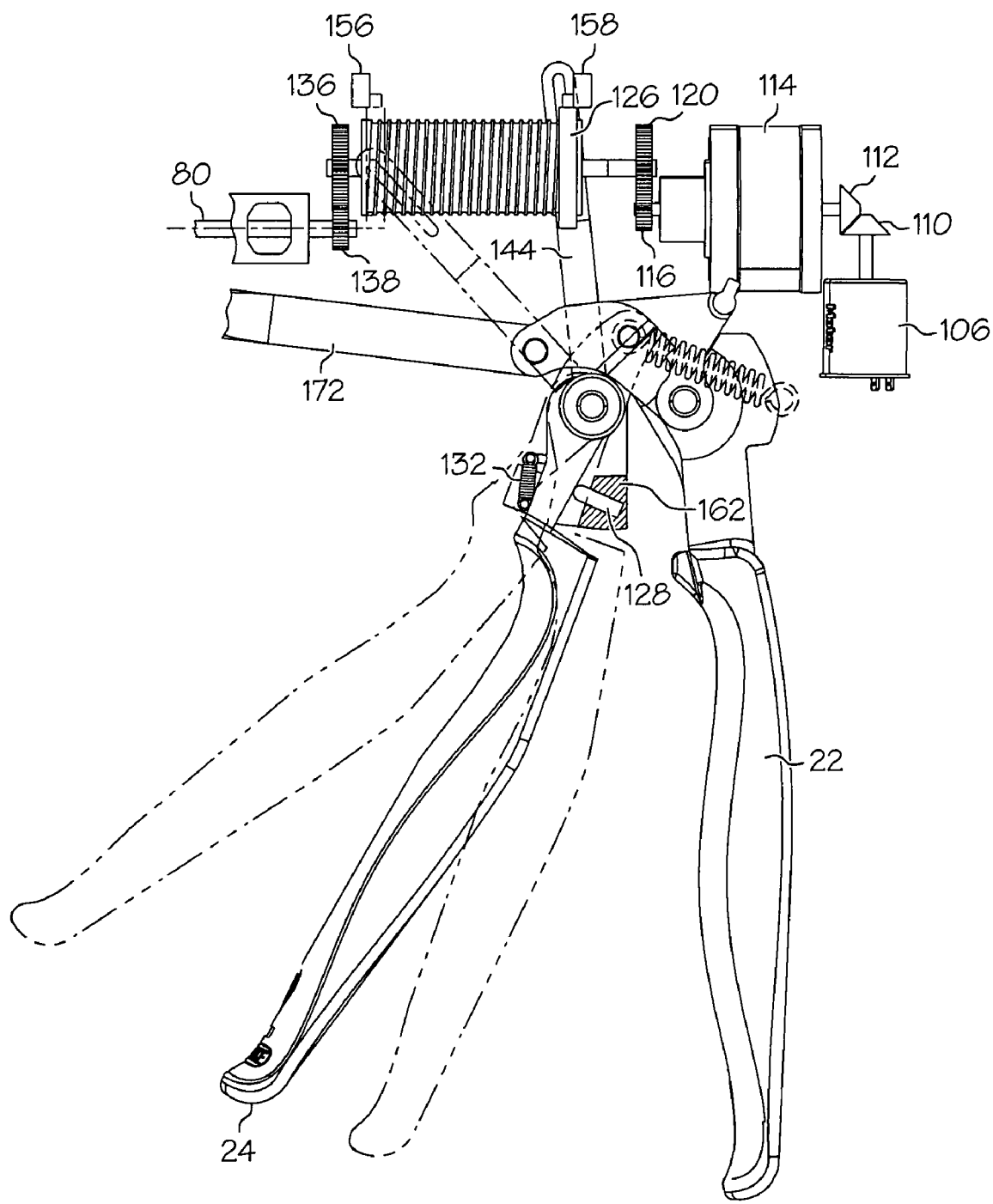
FIG. 10 is a side view of the handle according to various embodiments of the present invention.

The middle handle piece 130 includes a backside shoulder 160 that engages the slotted arm 144 as best shown in FIGS. 8 and 9. The middle handle piece 130 also has a forward motion stop 162 that engages the firing trigger 24. The movement of the slotted arm 144 is controlled, as explained above, by rotation of the motor 106. When the slotted arm 144 rotates CCW as the ring 126 travels from the proximate end of the helical gear drum 122 to the distal end, the middle handle piece 130 will be free to rotate CCW. Thus, as the operator draws in the firing trigger 24, the firing trigger 24 will engage the forward motion stop 162 of the middle handle piece 130, causing the middle handle piece 130 to rotate CCW. Due to the backside shoulder 160 engaging the slotted arm 144, however, the middle handle piece 130 will only be able to rotate CCW as far as the slotted arm 144 permits. In that way, if the motor 106 should stop rotating for some reason, the slotted arm 144 will stop rotating, and the operator will not be able to further draw in the firing trigger 24 because the middle handle piece 130 will not be free to rotate CCW due to the slotted arm 144.

Figure 11:
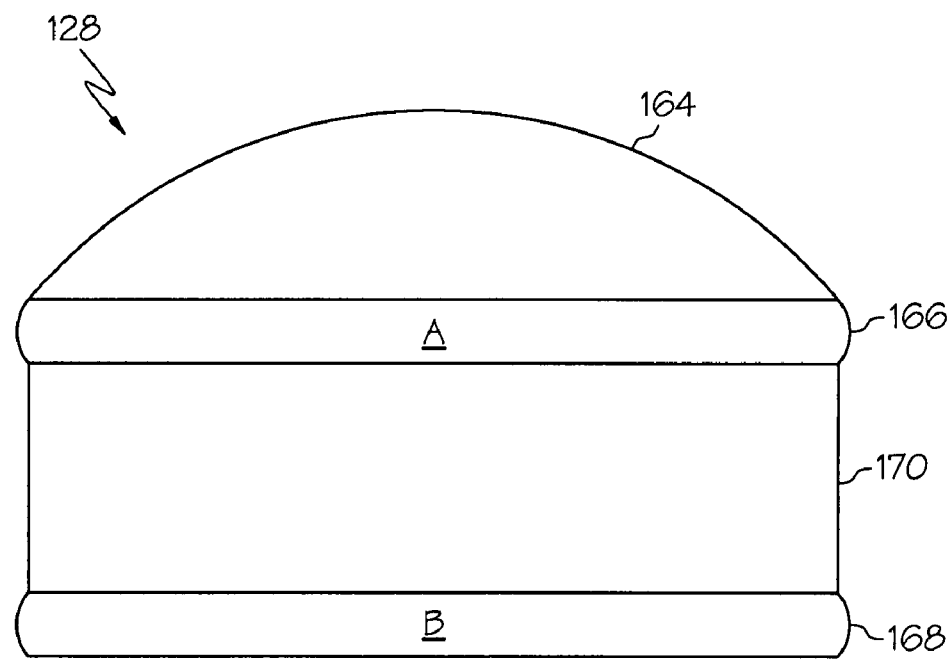
FIGS. 11-12 illustrate a proportional sensor that may be used according to various embodiments of the present invention.
Figure 12:
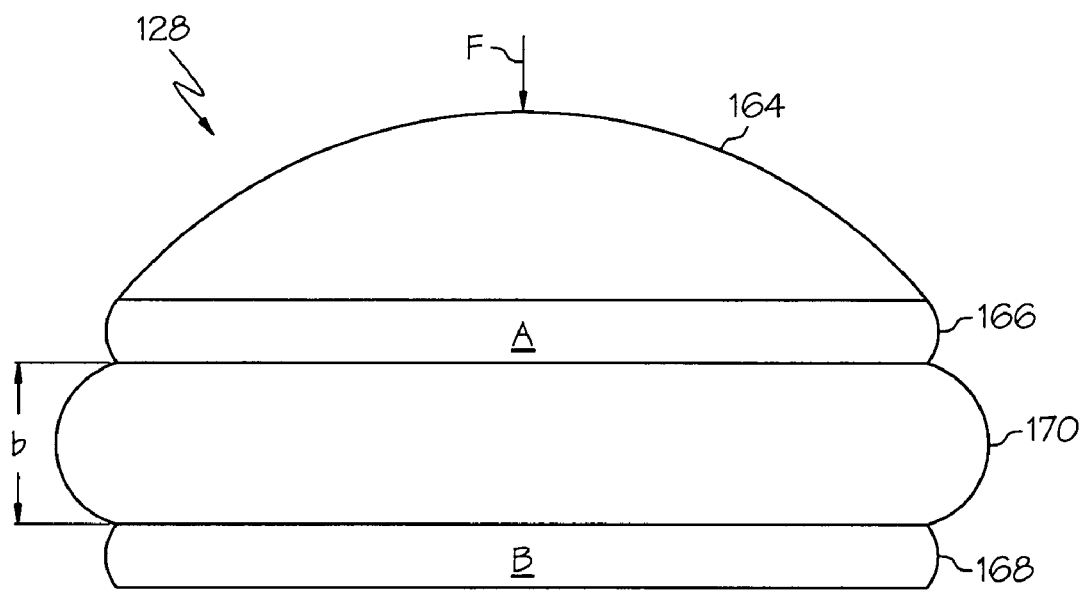

FIGS. 11 and 12 illustrate two states of a variable sensor that may be used as the run motor sensor 128 according to various embodiments of the present invention. The sensor 128 may include a face portion 164, a first electrode (A) 166, a second electrode (B) 168, and a compressible dielectric material 170 (e.g., EAP) between the electrodes 166, 168. The sensor 128 may be positioned such that the face portion 164 contacts the firing trigger 24 when retracted. Accordingly, when the firing trigger 24 is retracted, the dielectric material 170 is compressed, as shown in FIG. 12, such that the electrodes 166, 168 are closer together. Since the distance "b" between the electrodes 166, 168 is directly related to the impedance between the electrodes 166, 168, the greater the distance the more impedance, and the closer the distance the less impedance. In that way, the amount that the dielectric material 170 is compressed due to retraction of the firing trigger 24 (denoted as force "F" in FIG. 12) is proportional to the impedance between the electrodes 166, 168, which can be used to proportionally control the motor 106.

Components of an exemplary closure system for closing (or clamping) the anvil 28 of the end effector 16 by retracting the closure trigger 22 are also shown in FIGS. 7-10. In the illustrated embodiment, the closure system includes a yoke 172 connected to the closure trigger 22 by a pin 174 that is inserted through aligned openings in both the closure trigger 22 and the yoke 172. A pivot pin 176, about which the closure trigger 22 pivots, is inserted through another opening in the closure trigger 22 which is offset from where the pin 174 is inserted through the closure trigger 22. Thus, retraction of the closure trigger 22 causes the upper part of the closure trigger 22, to which the yoke 172 is attached via the pin 174, to rotate CCW. The distal end of the yoke 172 is connected, via a pin 178, to a first closure bracket 180. The first closure bracket 180 connects to a second closure bracket 182. Collectively, the closure brackets 180, 182 define an opening in which the proximal end of the proximate closure tube 72 (see FIG. 4) is seated and held such that longitudinal movement of the closure brackets 180, 182 causes longitudinal motion by the proximate closure tube 72. The instrument 10 also includes a closure rod 184 disposed inside the proximate closure tube 72. The closure rod 184 may include a window 186 into which a post 188 on one of the handle exterior pieces, such as exterior lower side piece 96 in the illustrated embodiment, is disposed to fixedly connect the closure rod 184 to the handle 12. In that way, the proximate closure tube 72 is capable of moving longitudinally relative to the closure rod 184. The closure rod 184 may also include a distal collar 190 that fits into a cavity 192 in proximate spine tube 79 and is retained therein by a cap 194 (see FIG. 4).

In operation, when the yoke 172 rotates due to retraction of the closure trigger 22, the closure brackets 180, 182 cause the proximate closure tube 72 to move distally (i.e., away from the handle 12 of the instrument 10), which causes the distal closure tube 74 to move distally, which causes the anvil 28 to rotate about the pivot point 42 into the clamped or closed position. When the closure trigger 22 is unlocked from the locked position, the proximate closure tube 72 is caused to slide proximally, which causes the distal closure tube 74 to slide proximally, which, by virtue of the tab 44 being inserted in the opening 78 of the distal closure tube 74, causes the anvil 28 to pivot about the pivot point 42 into the open or unclamped position. In that way, by retracting and locking the closure trigger 22, an operator may clamp tissue between the anvil 28 and channel 26, and may unclamp the tissue following the cutting/stapling operation by unlocking the closure trigger 22 from the locked position.

According to various embodiments, the instrument 10 may include an interlock for preventing instrument 10 operation when the staple cartridge 38 is not installed in the channel 26, or when the staple cartridge 38 is installed in the channel 26 but spent. Operation of the interlock is twofold. First, in the absence of an unspent staple cartridge 38 within the channel 26, the interlock operates to mechanically block distal advancement of the cutting instrument 34 through the channel 26 in response to actuation of the firing trigger 24. Using suitable electronics disposed within the handle 12, the interlock next detects the increase in current through the motor 106 resulting from the immobilized cutting instrument 34 and consequently interrupts current to the motor 106. Advantageously, the interlock eliminates the need for electronic sensors in the end effector 16, thus simplifying instrument design. Moreover, because the magnitude and duration of mechanical blocking force needed to produce the detected increase in motor current is significantly less than that which would be exerted if only a conventional mechanical interlock was used, physical stresses experienced by instrument components are reduced.

According to various embodiments, the interlock may include (1) a blocking mechanism to prevent actuation of the cutting instrument 34 by the motor 106 when an unspent staple cartridge 38 is not installed in the channel 26, and (2) a lockout circuit to detect the current through the motor 106 and to interrupt the current through the motor 106 based on the sensed current.

Figure 31:
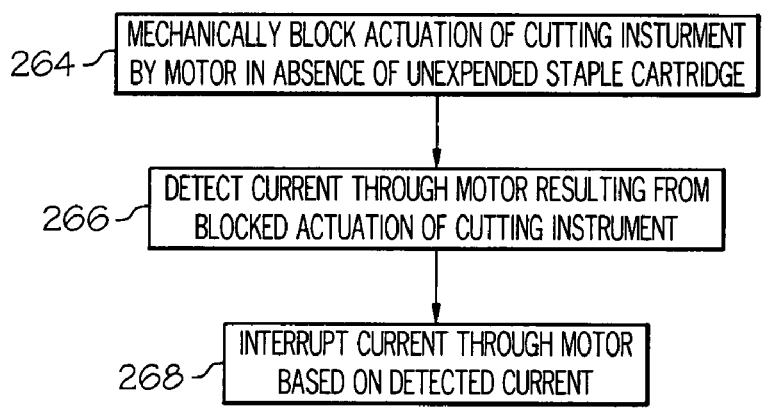
FIG. 31 is a flow diagram of a process implemented by an interlock according to various embodiments of the present invention.

FIG. 31 is a flow diagram of the process implemented by the interlock according to various embodiments. At step 264, the actuation of the cutting instrument 34 by the motor 106 is mechanically blocked by the blocking mechanism in the absence of an unspent staple cartridge 38 within the channel 26. As discussed below, the blocking mechanism may include components or features of conventional mechanical interlocks.

At step 266, the current through the motor 106 resulting from the blocked actuation of the cutting instrument 34 is detected by the lockout circuit. As discussed below, detection of the current may include, for example, the steps of sensing the motor current, generating a signal representative of the sensed motor current, and comparing the generated signal to a threshold signal.

At step 268, the current through the motor 106 is interrupted based on the detected current. Interrupting the current may include, for example, interrupting the current when the result of the comparison at step 266 indicates that the generated signal exceeds the threshold signal. Interrupting the current through the motor 106 may further include interrupting the current based on a position of the cutting instrument 34.

Figure 13:
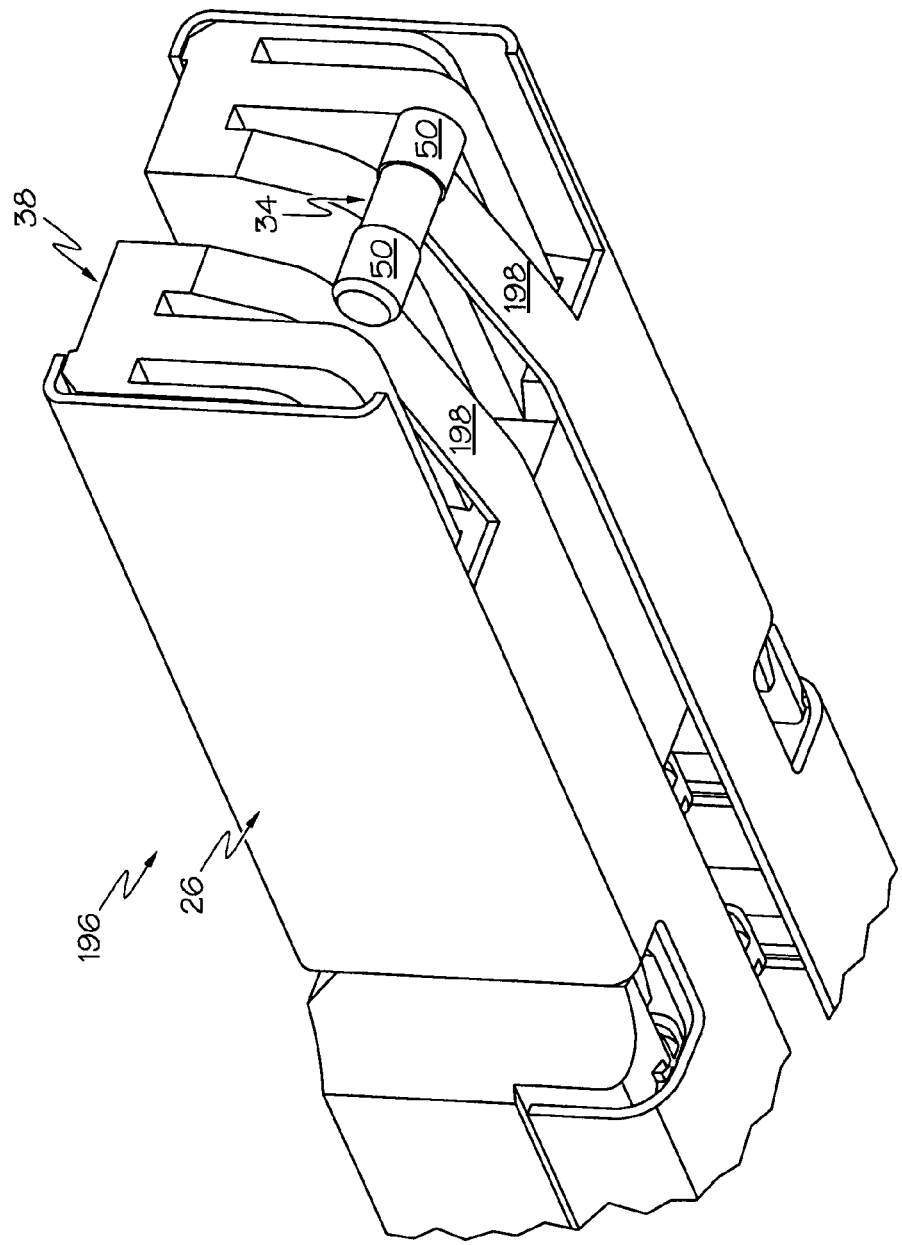
FIGS. 13-27 illustrate mechanical blocking mechanisms and the sequential operation of each according to various embodiments of the present invention.

According to various embodiments, the blocking mechanism of the interlock may include features similar or identical to those of conventional mechanical interlocks for physically blocking advancement of the cutting instrument 34 in the absence of an unspent staple cartridge 38 within the channel 26. FIG. 13 illustrates a blocking mechanism 196 according to one embodiment. The blocking mechanism 196 is disclosed in U.S. Pat. No. 7,044,352 entitled "SURGICAL STAPLING INSTRUMENT HAVING A SINGLE LOCKOUT MECHANISM FOR PREVENTION OF FIRING" to Shelton, IV et al., which is incorporated herein by reference. As shown, the blocking mechanism 196 may comprise a pair of spring fingers 198 positioned in the channel 26. In particular, the spring fingers 196 may raise up to block the middle pins 50 of the cutting instrument 34 when the sled 36 (not shown in FIG. 13) is not present in an unfired position at the proximal end of the channel 26, such as when the staple cartridge 38 is not installed or when the staple cartridge 38 is installed but spent. Although two spring fingers 198 are shown, it will be appreciated that more or fewer spring fingers 198 may be used instead.

Figure 14:
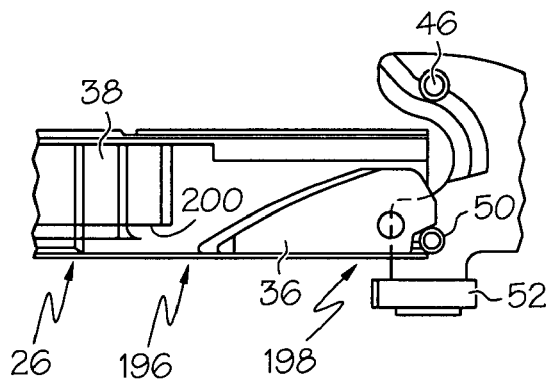

FIGS. 14-17 depict the operation of the spring fingers 198 sequentially as the instrument 10 is fired. In FIG. 14, an unspent staple cartridge 38 has been inserted into the channel 26. The presence of the sled 36 in its unfired position depresses the spring fingers 198 such that the firing drive slot 200 through which the middle pins 50 will pass is unimpeded.

Figure 15:
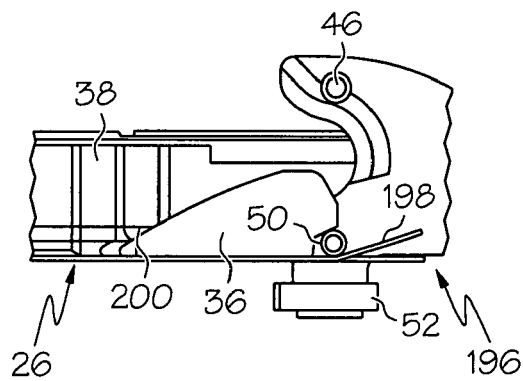

In FIG. 15, firing of the staple cartridge 38 has commenced, with the sled 36 and the middle pins 50 of the cutting instrument 34 having distally traversed off of the spring fingers 198, which then spring up into the firing drive slot 200.

Figure 16:
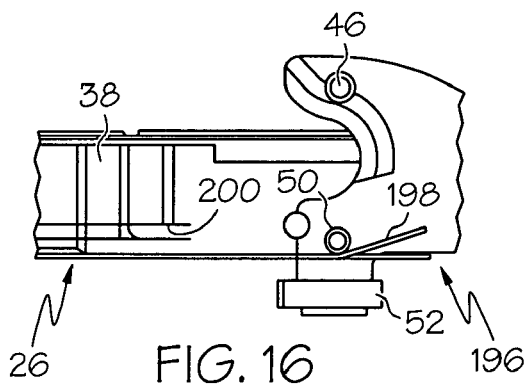

In FIG. 16, the staple cartridge 38 is now spent with the sled 36 fully driven distally and no longer depicted. The cutting instrument 34 is being retracted proximally. Since the spring fingers 198 pivot from a more distal point, the middle pins 50 of the cutting instrument 34 are able to ride up onto the spring fingers 198 during retraction, causing them to be depressed out of the firing drive slot 200.

Figure 17:
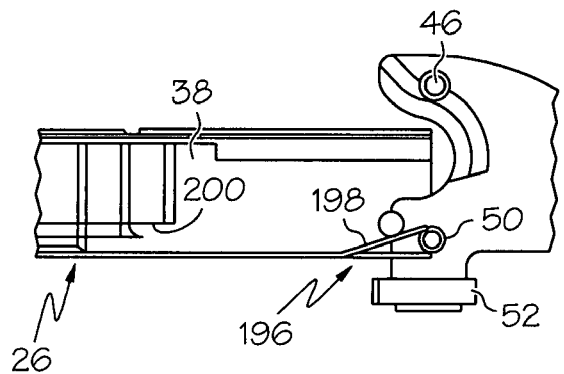

In FIG. 17, the cutting instrument 34 is fully retracted and now confronts the non-depressed pair of spring fingers 198 to prevent distal movement. The blocking mechanism 196 thereby remains activated until an unspent staple cartridge 38 is installed in the channel 26.

Figure 18:
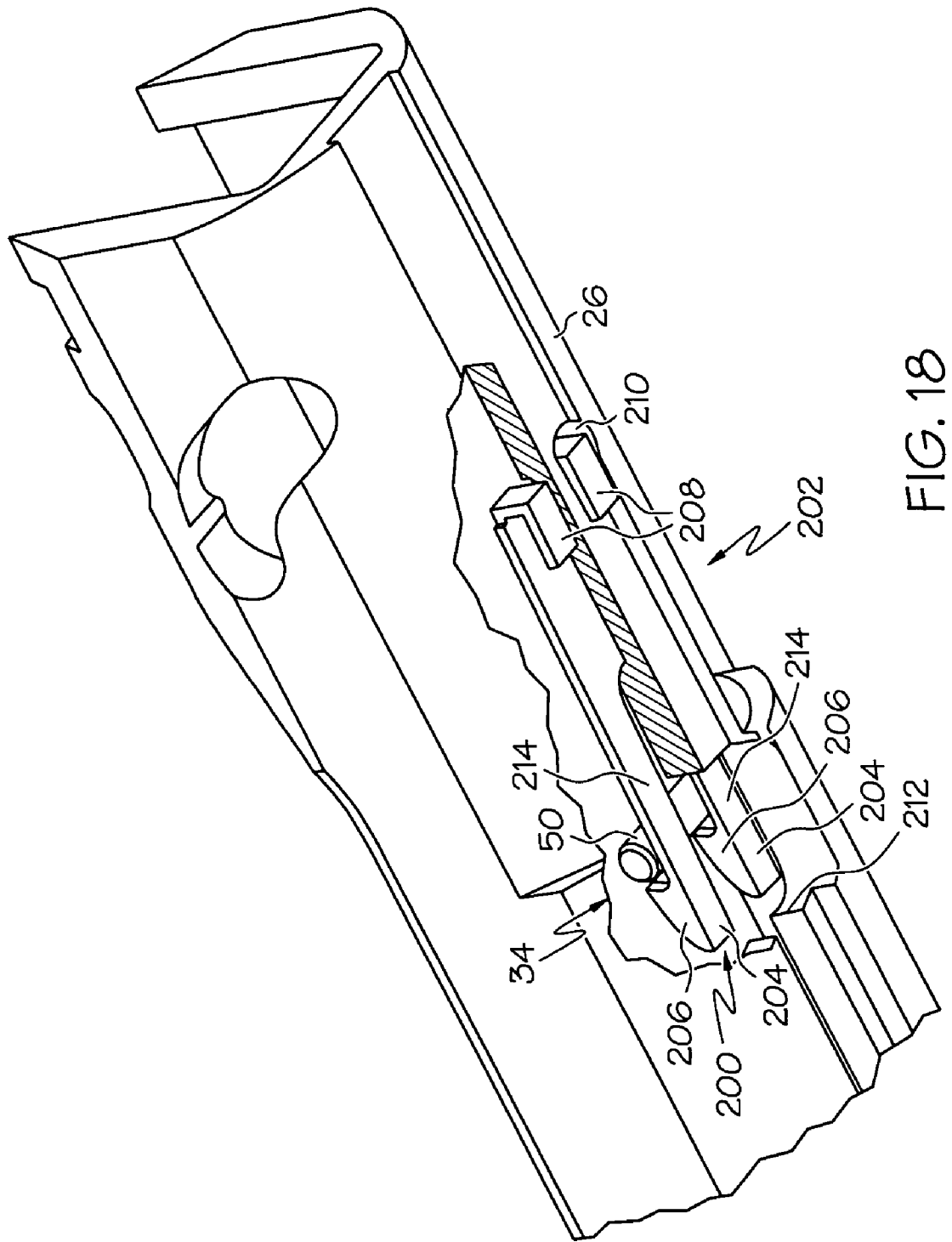

FIG. 18 depicts a blocking mechanism 202 according to another embodiment. The blocking mechanism 202, which is disclosed in U.S. Pat. No. 7,044,352 referenced above, includes a pair of hooks 204 having ramped ends 206 distally placed with regard to attachment devices 208. The attachment devices 208 are inserted through apertures 210 in the channel 26, thereby springedly attaching the hooks 204 to the channel 26. The ramped ends 206 lie above a hook recess 212 defined in the channel 26. Thus, when each ramped end 206 is contacted by the sled 36 of an unspent staple cartridge 38 (not shown in FIG. 18), the ramped ends 206 are depressed into the hook recess 212, thereby clearing the way for the middle pins 50 of the cutting instrument 34 to move distally through the firing drive slot 200 so that the staple cartridge 38 may be actuated. A thin shaft 214 coupling the attachment devices 208 respectively to the ramped end 206 of each hook 204 resiliently responds to absence of the sled 36, as depicted, wherein the ramped ends 206 return to impede the firing drive slot 200 to block the retracted middle pins 50 of the cutting instrument 34. Although two hooks 204 are shown, it will be appreciated that more or fewer hooks 204 may be used instead.

Figure 19:
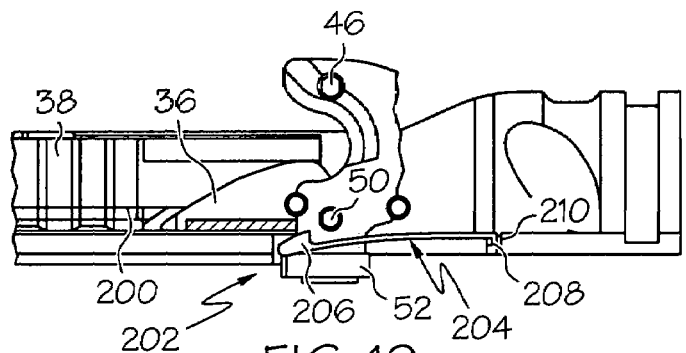
Figure 20:
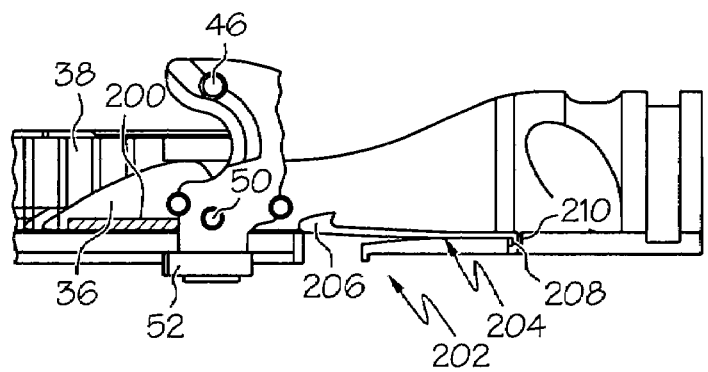

FIGS. 19-22 depict the sequence of operation of the hooks 204. In FIG. 19, the staple cartridge 38 is unspent so that the distally positioned sled 36 depresses the ramped ends 206 into the hook recess 212, allowing the middle pins 50 of the cutting instrument 34 to move distally through the firing drive slot 200 during firing, as depicted in FIG. 20. With the sled 36 and middle pins 50 distally removed with respect to the blocking mechanism 202, the ramped ends 206 resiliently raise out of the hook recess 212 to occupy the firing drive slot 200.

Figure 21:
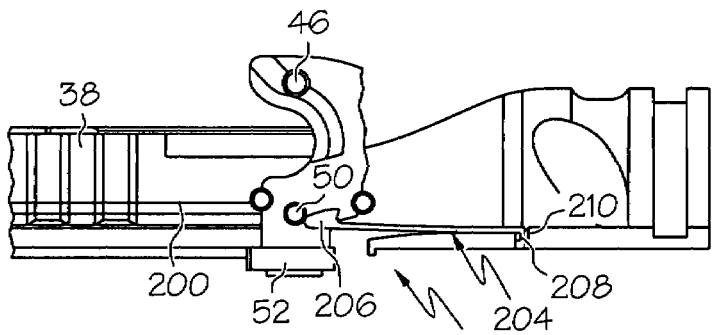
Figure 22:
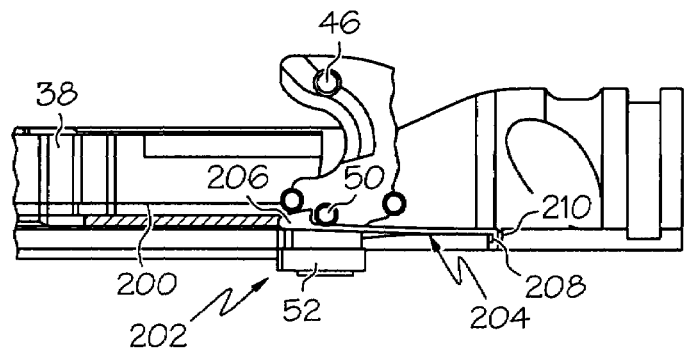

In FIG. 21, the cutting instrument 34 is being retracted to the point of contacting the ramped ends 206 of the hooks 204. Since the distal end of the ramped ends 206 is lower than the proximal part of the ramped ends 206, the middle pins 50 of the cutting instrument 34 ride over the ramped ends 206, forcing them down into the hook recess 212 until the middle pins 50 are past the ramped ends 206, as depicted in FIG. 22, wherein the ramped ends 206 resiliently spring back up to block the middle pins 50. Thus, the cutting instrument 34 is prevented from distal movement until an unspent staple cartridge 38 is installed in the channel 26.

Figure 23:
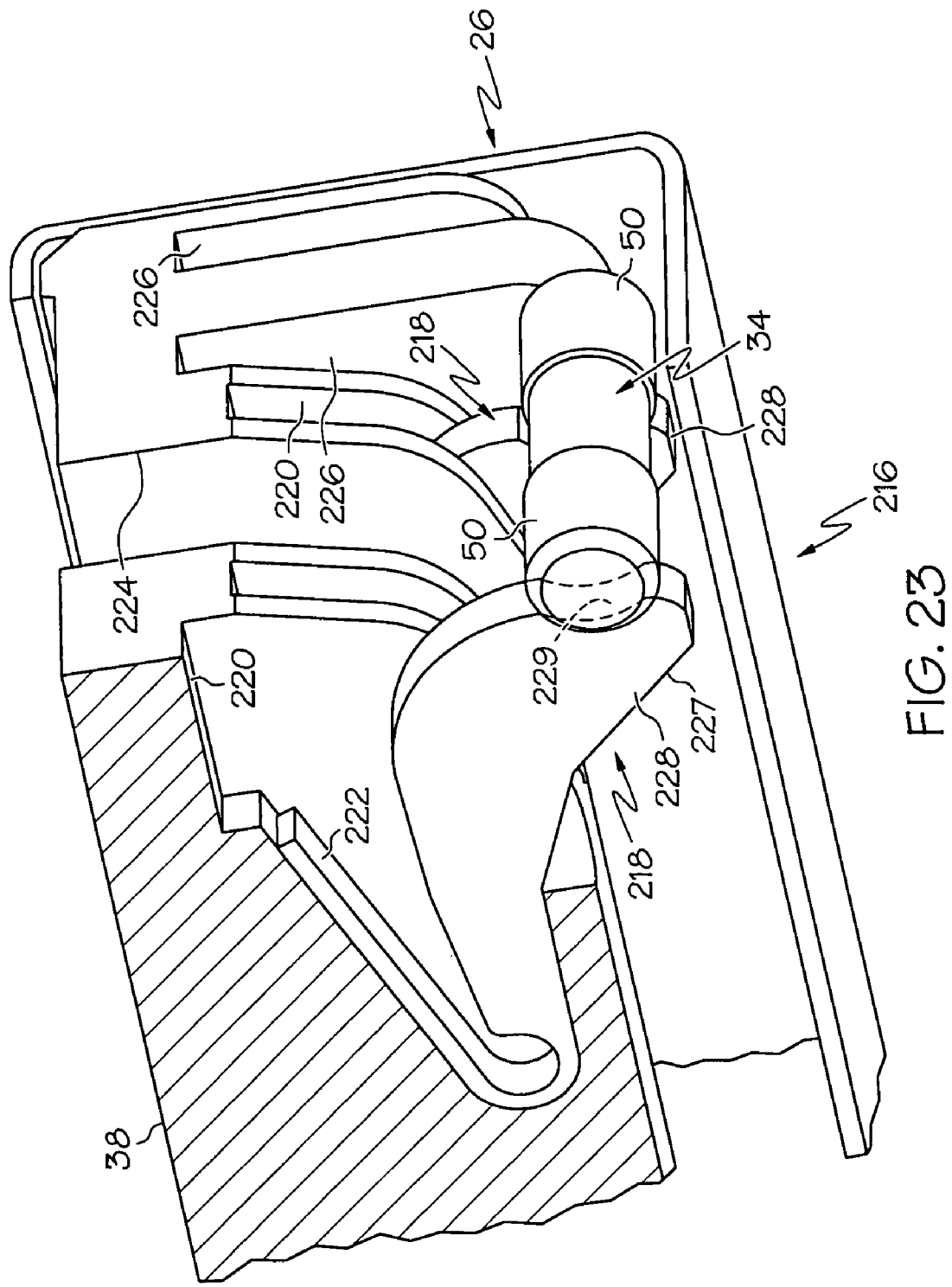

FIG. 23 depicts a blocking mechanism 216 according to yet another embodiment. The blocking mechanism 216 is disclosed in U.S. Pat. No. 6,988,649 entitled "SURGICAL STAPLING INSTRUMENT HAVING A SPENT CARTRIDGE LOCKOUT" to Shelton, IV et al., which is incorporated herein by reference. The blocking mechanism 216 is integrally formed with the staple cartridge 38 and includes proximally projecting blocking members 218 resiliently positioned above the sled 36 (not shown in FIG. 23). In particular, the blocking members 218 each reside within a downward and proximally opening cavity 220. Each blocking member 218 includes a leaf spring end 222 that is held within the cavity 220.

The cavities 220 are vertically aligned and spaced and parallel about a proximally presented vertical slot 224 in the staple cartridge 38 through which the cutting surface 56 (not shown in FIG. 23) passes. The staple cartridge 38 also includes slots 226 that longitudinally pass through the staple cartridge 38, being open from a portion of a proximal and underside of the staple cartridge 38 to receive the sled 36.

Each blocking member 218 has a deflectable end 228 having a ramped distal side 227 and blocking proximal side 229. The blocking members 218 are shaped to reside within their respective cavities 220 when depressed and to impede the distally moving middle pins 50 of the cutting instrument 34 when released.

Figure 24:
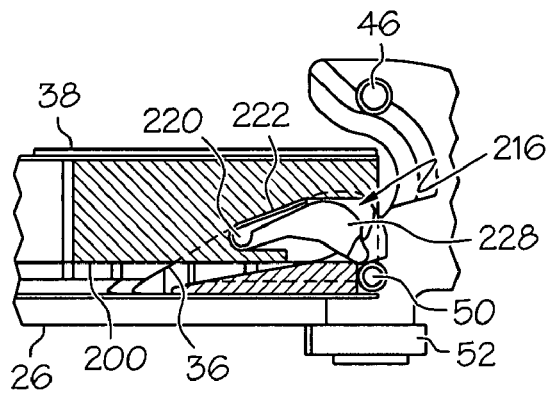

FIGS. 24-27 depict the blocking mechanism 216 sequentially as the instrument 10 is fired. In FIG. 24, an unspent staple cartridge 38 has been inserted into the channel 26 with the sled 36 depressing upward the deflectable ends 228 so that the firing drive slot 200 is unimpeded.

Figure 25:
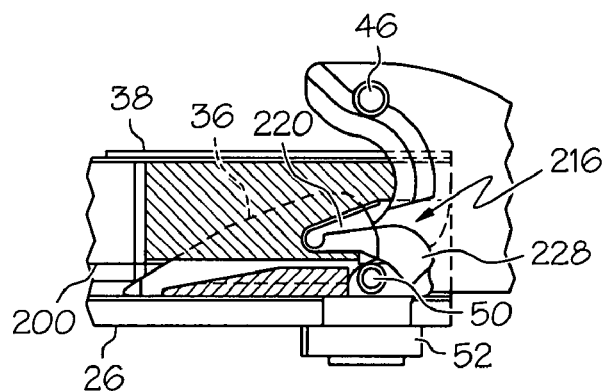

In FIG. 25, firing of the staple cartridge 38 has commenced, with the sled 36 and the middle pins 50 of the cutting instrument 34 having distally traversed past the deflectable ends 228, which then spring down into the firing drive slot 200.

Figure 26:
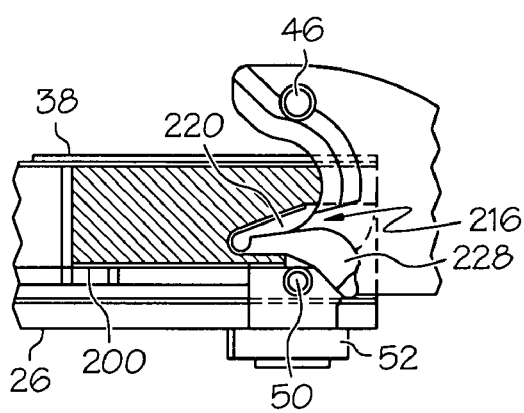

In FIG. 26, the staple cartridge 38 is now spent with the sled 36 fully driven distally and no longer depicted. The cutting instrument 34 is being retracted proximally. Since the deflectable ends 228 pivot from a more distal point, the middle pins 50 of the cutting instrument 34 are able to ride under the ramped distal sides 227 of the deflectable ends 228 during retraction, causing them to be depressed up, out of the firing drive slot 200.

Figure 27:
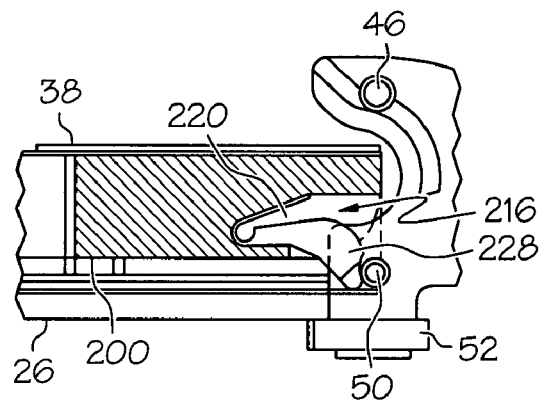

In FIG. 27, the cutting instrument 34 is fully retracted and the middle pints 50 now confront the blocking proximal sides 229 of the non-depressed (released) pair of deflectable ends 228 to prevent distal movement. The blocking mechanism 216 thereby remains activated until an unspent staple cartridge 38 is installed in the channel 26.

The blocking mechanisms 196, 202, 216 of the above-discussed embodiments are provided by way of example only. It will be appreciated that other suitable blocking mechanisms, such as blocking mechanisms disclosed in pending U.S. patent application Ser. No. 11/266,961 entitled "LOCKOUT MECHANISMS AND SURGICAL INSTRUMENTS INCLUDING SAME" to Ortiz et al., which is incorporated herein by reference, may be used instead.

Figure 28:
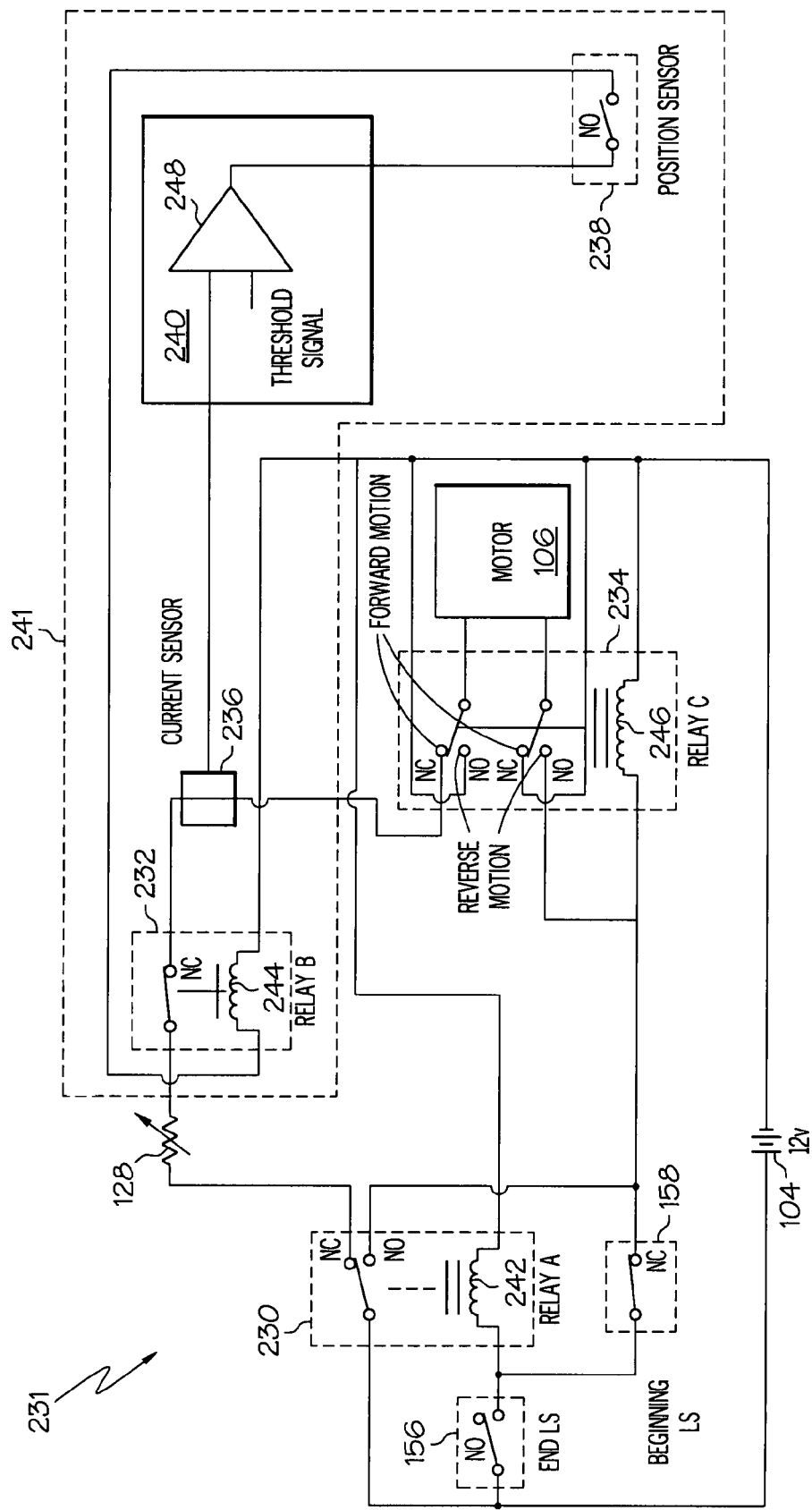
FIGS. 28-29 illustrate schematic diagrams of circuits used in the instrument according to various embodiments of the present invention.

FIG. 28 is a schematic diagram of an electrical circuit 231 of the instrument 10 according to various embodiments of the present invention. In certain embodiments, the circuit 231 may be housed within the handle 12. In addition to the sensor 128, sensors 156, 158 (depicted as a normally-open limit switch and a normally-closed limit switch, respectively), the battery 104, and the motor 106, the circuit 231 may include a single-pole double-throw relay 230, a single-pole single-throw relay 232, a double-pole double-throw relay 234, a current sensor 236, a position sensor 238, and a current detection module 240. Relay 232, the current sensor 236, the position sensor 238, and the current detection module 240 collectively form a lockout circuit 241. As described below, the lockout circuit 241 operates to sense the current through the motor 106 and to interrupt the current based upon the sensed current, thus "locking out" the instrument 10 by disabling its operation.

As described above, sensor 128 is activated when an operator pulls in the firing trigger 24 after locking the closure trigger 22. When switch 156 is open (indicating that the cutting/stapling operation of the end effector 16 is not yet complete), coil 242 of relay 230 is de-energized, thus forming a conductive path between the battery 104 and relay 232 via a normally-closed contact of relay 230. Coil 244 of relay 232 is controlled by the current detection module 240 and the position sensor 238 as described below. When coil 244 is de-energized and coil 242 is de-energized, a conductive path between the battery 104 and a normally-closed contact of relay 234 is formed. Relay 234 controls the rotational direction of the motor 106 based on the states of switches 156, 158. When switch 156 is open and switch 158 is closed (indicating that the cutting instrument 34 has not yet fully deployed distally), coil 246 of relay 234 is de-energized. Accordingly, when coils 242, 244, 246 are collectively de-energized, current from the battery 104 flows through the motor 106 via the normally-closed contacts of relay 234 and causes the forward rotation of the motor 106, which in turn causes distal deployment of the cutting instrument 34 as described above.

When switch 156 is closed (indicating that the cutting instrument 34 has fully deployed distally), coil 242 of relay 230 is energized, and coil 246 of relay 234 is energized via a normally-open contact of relay 230. Accordingly, current now flows to the motor 106 via normally-open contacts of relays 230, 234, thus causing reverse rotation of the motor 106 which in turn causes the cutting instrument 34 to retract from its distal position and switch 156 to open. Coil 242 of relay 230 remains energized until limit switch 158 is opened, indicating the complete retraction of the cutting instrument 34.

The magnitude of current through the motor 106 during its forward rotation is indicative of forces exerted upon the cutting instrument 34 during its deployment. As described above, the absence of an unspent staple cartridge 38 in the channel 26 (e.g., the presence of a spent staple cartridge 38 or the absence of a staple cartridge 38 altogether) results in activation of the blocking mechanism 196, 202, 216 such that distal movement of the cutting instrument 34 is prevented. The resistive force exerted by the blocking mechanism 196, 202, 216 against the cutting instrument 34 causes an increase in motor torque, thus causing motor current to increase to a level that is measurably greater than that present during a cutting and stapling operation. Accordingly, by sensing the current through the motor 106, the lockout circuit 241 may differentiate between deployment of the cutting instrument 34 when an unspent cartridge 38 is installed in the channel 26 versus deployment of the cutting instrument 34 when an unspent cartridge 38 is absent from the channel 26.

The current sensor 236 may be coupled to a path of the circuit 231 that conducts current to the motor 106 during its forward rotation. The current sensor 236 may be any current sensing device (e.g., a shunt resistor, a Hall effect current transducer, etc.) suitable for generating a signal (e.g., a voltage signal) representative of sensed motor current. The generated signal may be input to the current detection module 240 for processing therein, as described below.

According to various embodiments, the current detection module 240 may be configured for comparing the signal generated by the current sensor 236 to a threshold signal (e.g., a threshold voltage signal) to determine if the blocking mechanism 196, 202, 216 has been activated. For a given instrument 10, a suitable value of the threshold signal may be empirically determined a priori by, for example, measuring the peak signal generated by the current sensor 236 when the cutting instrument 34 is initially deployed (e.g., over the first 0.06 inches of its distal movement) during a cutting and stapling operation, and when the cutting instrument 34 is deployed and encounters the activated blocking mechanism 196, 202, 216. The threshold signal value may be selected to be less than the peak signal measured when the blocking mechanism 196, 202, 216 is activated, but larger than the peak signal measured during a cutting and stapling operation.

In certain embodiments and as shown in FIG. 28, the current detection module 240 may comprise a comparator circuit 248 for receiving the threshold and current sensor 236 signals and generating a discrete output based on a comparison of the received signals. For example, the comparator circuit 248 may generate a 5VDC output when the threshold signal is exceeded and a 0VDC output when the threshold signal is not exceeded. The threshold signal may be generated, for example, using a suitable signal reference circuit (e.g., a voltage reference circuit) (not shown). The design and operation of the comparator circuit 248 and signal reference circuit are well known in the art and are not described further herein.

The result of the threshold and current sensor 236 signal comparison is primarily of interest during the initial deployment (e.g., during the first 0.06 inches of distal movement) of the cutting instrument 34. Accordingly, the current detection module 240 may limit the comparison based on the distal position of the cutting instrument 34 as indicated by the position sensor 238. The position sensor 238 may be any type of position sensing device suitable for generating a signal indicative of a distal position of the cutting instrument 34. In one embodiment and as shown in FIG. 28, for example, the position sensor 238 may be a normally-open Hall effect position switch 238 that is actuated based on its proximity to a magnet mounted on the ring 126. The position switch 238 may mounted within the handle 12 and operate such that when the distal position of the cutting instrument 34 (as indicated by the position of ring 126) is within a pre-determined distance (e.g., distal position <0.06 inches) of its proximal-most position, the position switch 238 is closed. Conversely, when the distal position of the cutting instrument 34 exceeds the predetermined distance (e.g., distal position >0.06 inches), the position switch 238 is opened. The position switch 238 may be connected in series with the output of the comparator circuit 248 to limit the comparison based on the position of the cutting instrument 34. In this way, if the threshold signal is exceeded when the distal position of the cutting instrument 34 is greater than pre-determined distance, the output of the position switch 238 will remain at 0VDC (according to the example presented above), regardless of the result of the comparison. It will be appreciated that other types of position sensors 238 (e.g., mechanically-actuated limit switches, rotary potentiometers, etc.) may be used instead as an alternative to the Hall effect position switch 238 described above. Additionally, it will be appreciated that auxiliary contacts (not shown) of switch 158 may be used as an alternative to a separate position sensor 238. In embodiments in which the position sensor 238 does not include a switched output (e.g., when the position sensor 238 is a potentiometer or other analog-based position sensor), additional processing of the position sensor 236 output using, for example, a second comparator circuit, may be necessary.

As shown in FIG. 28, the output of the position switch 238 may be connected to coil 244 of relay 232. Driver circuitry (not shown) between the position switch 238 and the coil 244 may be provided if necessary. Accordingly, if the signal generated by the current sensor 236 exceeds the threshold signal (indicating activation of the blocking mechanism 196, 202, 216 due to the absence of an unspent staple cartridge 38), and the cutting instrument 34 is within the predetermined distance of its proximal-most position, coil 244 will be energized. This causes normally-closed switch of relay 232 to open, thereby interrupting current flow to the motor 106 and removing the resistive force exerted by the blocking mechanism 196, 202, 216 upon the cutting instrument 34. Importantly, because the blocking mechanism 196, 202, 216 need only apply a mechanical blocking force sufficient to cause the threshold signal to be exceeded, the physical stresses exerted by the blocking mechanism 196, 202, 216 are reduced in magnitude and duration compared to those that would be exerted if only conventional mechanical interlocks were used. Furthermore, because the interlock does not require electronic sensors in the end effector 16, instrument design is simplified.

Figure 29:
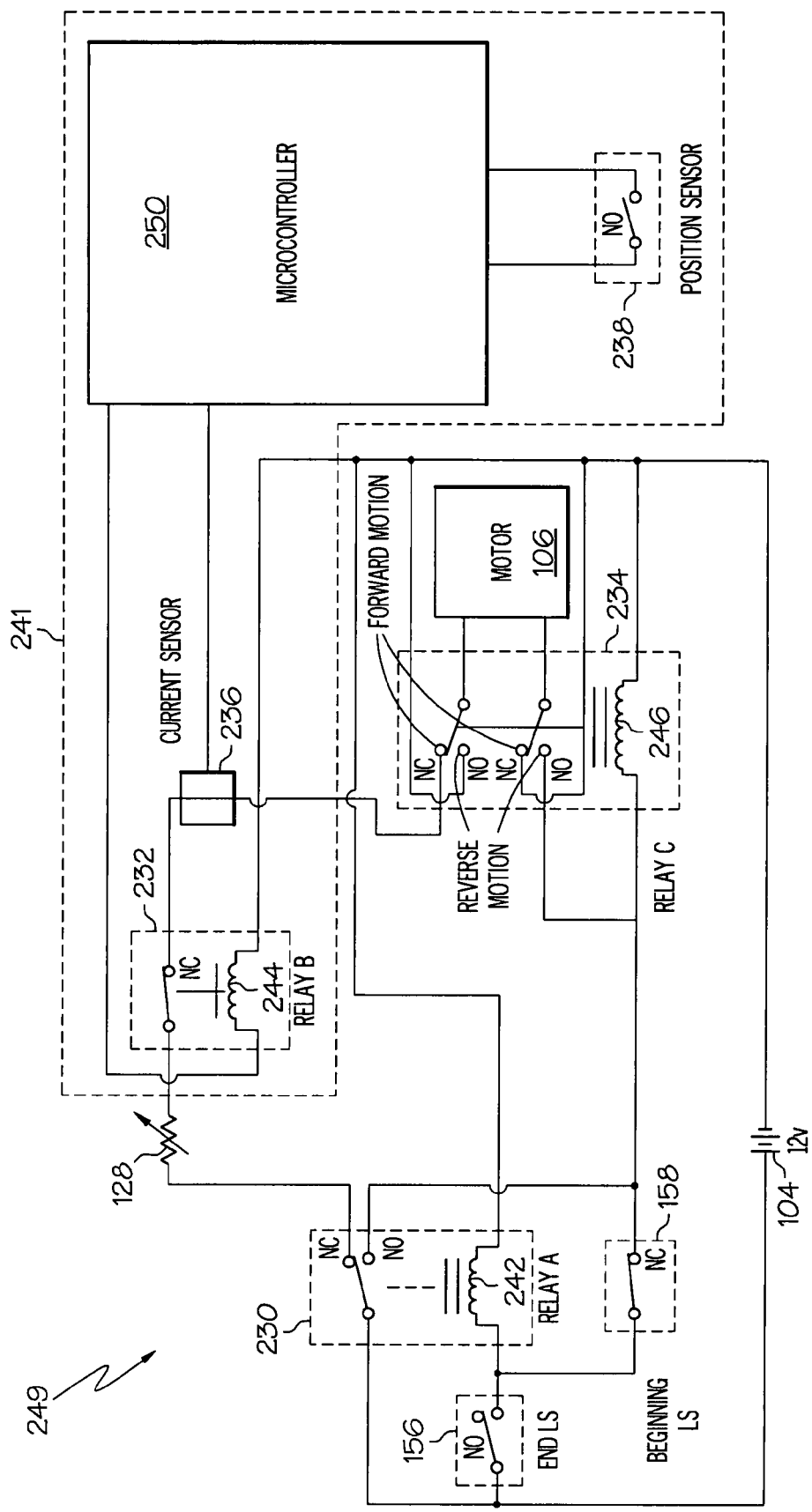

FIG. 29 is a schematic diagram of an electrical circuit 249 of the instrument 10 according to another other embodiment of the present invention in which a processor-based microcontroller 250 is used to implement functionality of the lockout circuit 241 described above. Although not shown for purposes of clarity, the microcontroller 250 may include components well known in the microcontroller art such as, for example, a processor, a random access memory (RAM) unit, an erasable programmable read-only memory (EPROM) unit, an interrupt controller unit, timer units, analog-to-digital conversion (ADC) and digital-to-analog conversion (DAC) units, and a number of general input/output (I/O) ports for receiving and transmitting digital and analog signals. The current sensor 236 and the position sensor 238 may be connected to analog and digital inputs, respectively, of the microcontroller 250, and the coil 244 of relay 232 may be connected to a digital output of the microcontroller 250. It will be appreciated that in embodiments in which the output of the position sensor 238 is an analog signal, the position sensor 238 may be connected to an analog input instead. Additionally, although the circuit 249 of FIG. 29 includes relays 230, 232, 234, it will be appreciated that in other embodiments the relay switching functionality may be replicated using solid state switching devices, software, and combinations thereof. In certain embodiments, for example, instructions stored and executed in the microcontroller 250 may be used to control solid state switched outputs of the microcontroller 250. In such embodiments, switches 156, 158 may be connected to digital inputs of the microcontroller 250.

Figure 30:
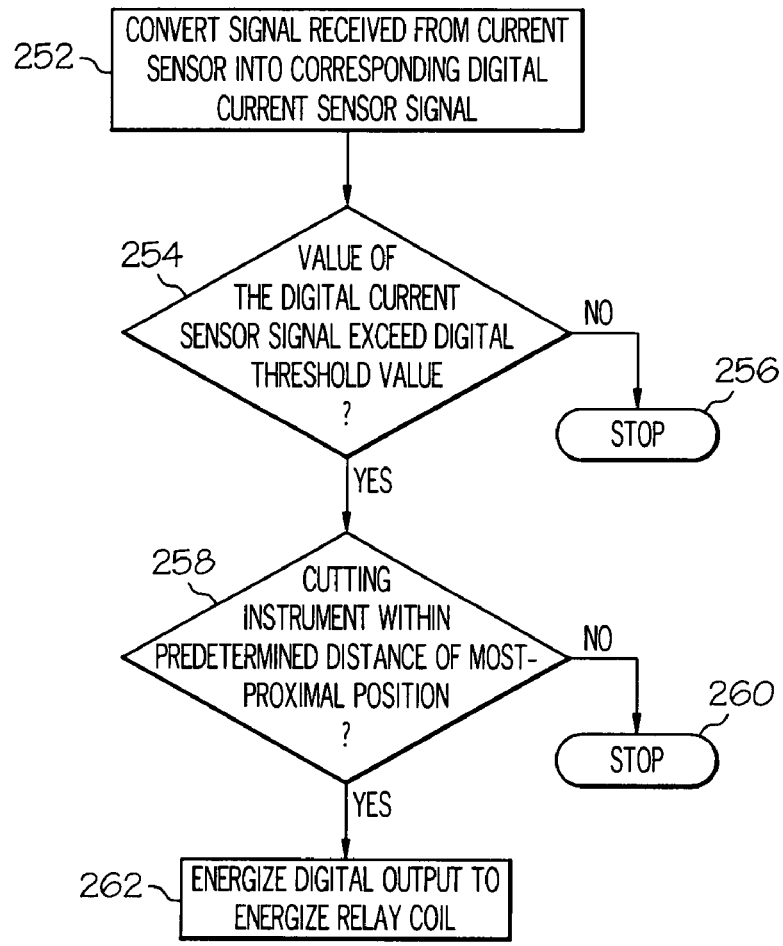
FIG. 30 is a flow diagram of a process implemented by the microcontroller of FIG. 29 according to various embodiments of the present invention.

FIG. 30 is a flow diagram of a process implemented by the microcontroller 250 according to various embodiments. At step 252, the microcontroller 250 receives the signal generated by the current sensor 236 via an analog input and converts the received signal into a corresponding digital current sensor signal.

At step 254, values of the digital current sensor signal are compared to a digital threshold value stored within the microcontroller 250. The digital threshold value may be, for example, a digitized representation of the threshold signal discussed above in connection with FIG. 28. If all values of the digital current sensor signal are less than the digital threshold value, the process terminates at step 256. If a value of the digital current sensor signal exceeds the digital threshold value, the process proceeds to step 258.

At step 258, the position sensor 238 input is processed to determine if the cutting instrument 34 is within the predetermined distance of its proximal-most position. If the cutting instrument 34 is not within the predetermined distance, the process is terminates at step 260. If the cutting instrument 34 is within the predetermined distance, the process proceeds to step 262.

At step 262, the digital output to corresponding to coil 244 is energized, thus causing the normally closed contacts of relay 232 to open, which in turn interrupts the current flow to the motor 106.

Although embodiments described above compare the magnitude of the current sensor signal (or a digitized version thereof) to a threshold signal or value, it will be appreciated that other metrics for analyzing the current sensor signal may additionally or alternatively be used to differentiate between deployment of the cutting instrument 34 when an unspent cartridge 38 is installed in the channel 26 versus deployment of the cutting instrument 34 when an unspent cartridge 38 is absent from the channel 26. For example, the current detection module 240 or the microcontroller 250 may be configured to determine derivative and/or integral characteristics of the current sensor signal for comparison to corresponding thresholds signals or values. Additionally, in certain embodiments the current sensor signal may be processed prior to its analysis using, for example, signal conditioners and/or filters implementing one or more filter response functions (e.g., infinite impulse response functions).

The various embodiments of the present invention have been described above in connection with cutting-type surgical instruments. It should be noted, however, that in other embodiments, the inventive surgical instrument disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   an end effector comprising:
      a cutting instrument actuable to cut an object;
      a longitudinally extending channel, the channel having a proximal end and a distal end;
      an anvil pivotally attached to the channel, wherein the object is positionable between the anvil and the channel;
      a staple cartridge removably seated in the channel, the staple cartridge having a proximal end and a distal end;
      a firing drive slot formed between the cartridge and the channel through which at least a portion of the cutting instrument passes when the cutting instrument is actuated; and
      a sled disposed in the staple cartridge, wherein when the cutting instrument is actuated the sled is engaged by the cutting instrument and driven longitudinally through the staple cartridge from an unfired position located at the proximal end of the staple cartridge to a fired position located at the distal end of the staple cartridge;
   a motor coupled to the end effector to actuate the cutting instrument; and
   an interlock coupled to the end effector and to the motor, the interlock to prevent actuation of the cutting instrument based on a current through the motor, the interlock comprising:
      a blocking mechanism to prevent actuation of the cutting instrument when the sled is not present in the unfired position; and
      a lockout circuit to sense the current through the motor and to interrupt the current through the motor based on the sensed current.

2. The instrument of claim 1, wherein the lockout circuit is further to interrupt the current through the motor based on a position of the cutting instrument.

3. The instrument of claim 1, wherein the current through the motor increases when the blocking mechanism prevents the cutting instrument from advancing longitudinally through the channel.

4. The instrument of claim 1, wherein the blocking mechanism comprises at least one spring finger disposed in the channel.

5. The instrument of claim 1, wherein the blocking mechanism comprises at least one ramped hook springedly attached to the channel.

6. The instrument of claim 1, wherein the blocking mechanism is formed integrally with the staple cartridge and comprises at least one proximally projecting member, wherein the at least one member is movable between the firing drive slot and a recess in the staple cartridge.

7. The instrument of claim 1, wherein the lockout circuit comprises a current sensor to generate a first signal representative of the sensed current.

8. The instrument of claim 7, wherein the lockout circuit further comprises a current detection module to compare the first signal to a predetermined threshold signal.

9. The instrument of claim 8, wherein the current detection module comprises a microprocessor.

10. The instrument of claim 8, wherein the lockout circuit further comprises a position sensor to determine a position of the cutting instrument.

11. The instrument of claim 10, wherein the lockout circuit further comprises a switch connected in series with the motor, the switch controllable to interrupt the current through the motor based on the position of the cutting instrument and the comparison of the first signal to the predetermined threshold signal.

12. The instrument of claim 11, wherein the switch is controllable to interrupt the current through the motor when the position of the cutting instrument is within a predetermined distance of the proximal-most position of the cutting instrument and when the first signal exceeds the predetermined threshold signal.

* * * * *

UNITED STATES PATENT AND TRADEMARK OFFICE
CERTIFICATE OF CORRECTION

Page 1 of 1

PATENT NO.        : 7,721,936 B2
APPLICATION NO.   : 11/651788
DATED             : May 25, 2010
INVENTOR(S)       : Frederick E. Shelton, IV and James R. Giordano It is certified that error appears in the above-identified patent and that said Letters Patent is hereby corrected as shown below:

Title Page item [75]
Error in
Inventors Last Name "Frederick E. Shalton, IV"

Title Page item [75]
Correct to
Inventors Last Name "Frederick E. Shelton, IV"

Signed and Sealed this
Twenty-seventh Day of March, 2012

David J. Kappos
*Director of the United States Patent and Trademark Office*